「(12) United States Patent
Ogino et al.

(10) Patent No.: US 10,314,791 B2
(45) Date of Patent: Jun. 11, 2019

(54) ADHESIVE SHEET FOR ATTACHMENT TO SKIN AND PERCUTANEOUS ABSORPTION PREPARATION USING SAME

(71) Applicant: KM Transderm Ltd., Osaka-shi, Osaka (JP)

(72) Inventors: Hiroyuki Ogino, Higashikagawa (JP); Sadao Yukimoto, Higashikagawa (JP); Atsuyo Hamada, Higashikagawa (JP); Mitsuji Akazawa, Higashikagawa (JP); Masaoki Goto, Higashikagawa (JP)

(73) Assignee: KM Transderm Ltd., Osaka (JP)

( * ) Notice: Subject to any disclaimer, the term of this patent is extended or adjusted under 35 U.S.C. 154(b) by 0 days.

(21) Appl. No.: 15/533,154

(22) PCT Filed: Dec. 4, 2015

(86) PCT No.: PCT/JP2015/084221
§ 371 (c)(1),
(2) Date: Aug. 7, 2017

(87) PCT Pub. No.: WO2016/088898
PCT Pub. Date: Jun. 9, 2016

(65) Prior Publication Data
US 2017/0333367 A1    Nov. 23, 2017

(30) Foreign Application Priority Data
Dec. 5, 2014   (JP) .................................. 2014-261231

(51) Int. Cl.
| | |
|---|---|
| *A61K 9/70* | (2006.01) |
| *A61K 31/27* | (2006.01) |
| *A61K 47/06* | (2006.01) |
| *A61K 47/32* | (2006.01) |

(52) U.S. Cl.
CPC .......... *A61K 9/7007* (2013.01); *A61K 9/7053* (2013.01); *A61K 31/27* (2013.01); *A61K 47/06* (2013.01); *A61K 47/32* (2013.01)

(58) Field of Classification Search
None
See application file for complete search history.

(56) References Cited

U.S. PATENT DOCUMENTS

| | | | |
|---|---|---|---|
| 5,274,036 A | 12/1993 | Korpman et al. | |
| 5,770,221 A | 6/1998 | Nakamura et al. | |
| 9,895,320 B2 * | 2/2018 | Ogino ................. | A61K 9/7084 |
| 2013/0226112 A1 | 8/2013 | Akazawa et al. | |
| 2015/0374642 A1 | 12/2015 | Ogino et al. | |

FOREIGN PATENT DOCUMENTS

| | | | | |
|---|---|---|---|---|
| EP | 2614819 A1 | 7/2013 | | |
| JP | S61-040215 A | 2/1986 | | |
| JP | H08-506127 A | 7/1996 | | |
| JP | H09-291028 A | 11/1997 | | |
| JP | H10-316559 A | 12/1998 | | |
| JP | 2001-302502 A | 10/2001 | | |
| JP | 2012149061 A * | 8/2012 | .......... | A61K 31/192 |
| WO | WO 1995/031190 A1 | 11/1995 | | |
| WO | WO 2012/029325 A1 | 3/2012 | | |
| WO | WO 2014/051128 A1 | 4/2014 | | |
| WO | WO 2014/111790 A2 | 7/2014 | | |

OTHER PUBLICATIONS

Nara, Masato, "Nenchaku Seihin No Oyo Gijutsu" ["Applied Technology of Adhesive Product"], Chapter 4 ("Application of Adhesive Products"), Section 3 ("Adhesive Products for Medical Use"), pp. 125-141 (Keiji Fukuzawa et al., eds., CMC Publishing Co., Ltd., 2000).
Japanese Patent Office, International Search Report in International Patent Application No. PCT/JP2015/084221 (dated Jan. 19, 2016).

* cited by examiner

*Primary Examiner* — Aradhana Sasan
(74) *Attorney, Agent, or Firm* — Leydig, Voit & Mayer, Ltd.

(57) ABSTRACT

The invention provides an adhesive sheet for skin, which shows sufficient adhesiveness to the skin and causes low skin irritation. The adhesive sheet contains an adhesive layer formed on a support, in which the adhesive layer contains at least a thermoplastic elastomer, a non-volatile hydrocarbon oil, and polyisobutylene, but no tackifier. The polyisobutylene is a medium molecular weight polyisobutylene with a viscosity average molecular weight of more than 100,000 and not more than 500,000. The invention also provides a percutaneous absorption preparation containing a drug or a pharmaceutically acceptable salt thereof in an adhesive layer of the inventive adhesive sheet for skin.

16 Claims, No Drawings

ADHESIVE SHEET FOR ATTACHMENT TO SKIN AND PERCUTANEOUS ABSORPTION PREPARATION USING SAME

CROSS-REFERENCE TO RELATED APPLICATIONS

This patent application is the U.S. national phase of International Patent Application No. PCT/JP2015/084221, filed on Dec. 4, 2015, which claims the benefit of Japanese Patent Application No. 2014-261231, filed Dec. 5, 2014, the disclosures of which are incorporated herein by reference in their entireties for all purposes.

TECHNICAL FIELD

The present invention relates to an adhesive sheet for skin, which shows sufficient adhesiveness to the skin and causes low skin irritation, and a percutaneous absorption preparation having sufficient skin permeability of a drug and sufficient adhesiveness to the skin, and causing low skin irritation.

BACKGROUND ART

When percutaneous absorption of a drug is desired, the drug is added to an adhesive base and the like and a patch is foamed. In recent years, a tape agent more superior in the adhesiveness is more often used than cataplasm containing a large amount of water as a constituent component in the patch. As the adhesive base for this tape agent, lipophilic adhesive bases such as rubber-based, acrylic-based, silicone-based and the like are used. Of these, rubber adhesive bases are widely used since they permit easy blending of additive as compared to other adhesive bases (patent documents 1-3).

However, problems in that sufficient releasability of the drug cannot be ensured, skin irritation caused by a tackifier generally added to a percutaneous absorption preparation is developed and the like have also been pointed out for a percutaneous absorption preparation using a rubber adhesive base.

Under the circumstances, the present inventors have found that an adhesive sheet for skin, which shows sufficient adhesiveness and causes low skin irritation can be obtained even without using a tackifier but by using a thermoplastic elastomer and a large amount of liquid paraffin relative to the elastomer, and that a percutaneous absorption preparation having sufficient percutaneous absorbability can be obtained by containing a drug or a pharmaceutically acceptable salt thereof in the adhesive sheet (patent document 4).

However, in some cases, the adhesiveness is somewhat insufficient to cause peeling and lifting of an end part, when perspiration is high, when attaching continues for a long time, when the movement around the attached part is large and the like.

DOCUMENT LIST

Patent Documents patent document 1: JP-A-2001-302502
patent document 2: JP-A-9-291028
patent document 3: JP-A-10-316559
patent document 4: WO 2012/029325

Non-Patent Document non-patent document 1: "NENCHAKU SEIHIN NO OYO GIJUTSU (Applied technology of adhesive product)" pp. 125-141, Keiji Fukuzawa et al., CMC Publishing Co., Ltd., 2000

SUMMARY OF THE INVENTION

Problems to be Solved by the Invention

An object of the present invention is to provide an adhesive sheet for skin, which shows sufficient adhesiveness to the skin and causes low skin irritation, and a percutaneous absorption preparation having sufficient skin permeability of a drug and sufficient adhesiveness to the skin, and causing low skin irritation.

Means of Solving the Problems

The present inventors have conducted intensive studies in an attempt to solve the aforementioned problem, and found that an adhesive sheet for skin having sufficient adhesiveness to the skin and causing low skin irritation can be obtained even without containing a tackifier but by using, as an adhesive base, a thermoplastic elastomer, non-volatile hydrocarbon oil and polyisobutylene having a viscosity average molecular weight of more than 100,000 and not more than 500,000.

In addition, they have found that an adhesive sheet for skin, which shows sufficient adhesiveness to the skin and causes low skin irritation can be obtained even without containing a tackifier but by using, as an adhesive base, a thermoplastic elastomer, a large amount of non-volatile hydrocarbon oil relative to the elastomer, and low molecular weight and high molecular weight polyisobutylenes.

Furthermore, they have found that a percutaneous absorption preparation having sufficient skin permeability can be obtained by containing a drug or a pharmaceutically acceptable salt thereof in the above-mentioned adhesive sheet, which resulted in the completion of the present invention.

Accordingly, the present invention relates to the following [1]-[16].

[1] An adhesive sheet for skin comprising a support and an adhesive layer formed on the support, wherein the adhesive layer comprises at least a thermoplastic elastomer, non-volatile hydrocarbon oil and polyisobutylene having a viscosity average molecular weight of more than 100,000 and not more than 500,000, a content of the non-volatile hydrocarbon oil is more than 120 parts by weight and not more than 800 parts by weight, per 100 parts by weight of the above-mentioned elastomer, and a content of the above-mentioned polyisobutylene is more than 3 parts by weight and not more than 500 parts by weight, per 100 parts by weight of the above-mentioned elastomer, and a tackifier is not contained.

[2] The adhesive sheet for skin of the above-mentioned [1], wherein the content of the polyisobutylene is more than 10 parts by weight and not more than 300 parts by weight, per 100 parts by weight of the thermoplastic elastomer.

[3] The adhesive sheet for skin of the above-mentioned [2], wherein the content of the polyisobutylene is more than 20 parts by weight and not more than 100 parts by weight, per 100 parts by weight of the thermoplastic elastomer.

[4] The adhesive sheet for skin of any one of the above-mentioned [1]-[3], wherein the thermoplastic elastomer is a mixture of a triblock copolymer and a diblock copolymer, and a content of the diblock copolymer in the mixture is not less than 20 wt %.

[5] The adhesive sheet for skin of the above-mentioned [4], wherein the content of the diblock copolymer in the mixture is not less than 30 wt %.

[6] The adhesive sheet for skin of any one of the above-mentioned [1]-[5], wherein the thermoplastic elastomer is a styrene-based block copolymer.

[7] The adhesive sheet for skin of the above-mentioned [6], wherein the styrene-based block copolymer is a mixture of a styrene-isoprene-styrene block copolymer and a styrene-isoprene block copolymer.

[8] The adhesive sheet for skin of any one of the above-mentioned [1]-[7], wherein a 25 wt % toluene solution of the thermoplastic elastomer has a solution viscosity at 25° C. of not less than 0.5 Pa·s.

[9] The adhesive sheet for skin of the above-mentioned [8], wherein the 25 wt % toluene solution of the thermoplastic elastomer has a solution viscosity at 25° C. of not less than 0.7 Pa·s.

[10] The adhesive sheet for skin of any one of the above-mentioned [1]-[9], wherein the non-volatile hydrocarbon oil has a kinematic viscosity at 40° C. of not less than 80 mm$^2$/s.

[11] The adhesive sheet for skin of any one of the above-mentioned [1]-[10], wherein the content of the non-volatile hydrocarbon oil in the adhesive layer is not less than 30 wt % and not more than 80 wt %.

[12] A percutaneous absorption preparation comprising the adhesive sheet for skin of any one of the above-mentioned [1]-[11], and a drug or a pharmaceutically acceptable salt thereof comprised in the adhesive layer of the adhesive sheet.

[13] The percutaneous absorption preparation of the above-mentioned [12], wherein the drug is rivastigmine.

[14] An adhesive sheet for skin comprising a support and an adhesive layer formed on the support, wherein
the adhesive layer comprises
at least a thermoplastic elastomer, non-volatile hydrocarbon oil and polyisobutylene having a viscosity average molecular weight of more than 100,000 and not more than 500,000, and
a tackifier is not contained.

[15] A percutaneous absorption preparation comprising the adhesive sheet for skin of the above-mentioned [14], and a drug or a pharmaceutically acceptable salt thereof comprised in the adhesive layer of the adhesive sheet.

[16] The percutaneous absorption preparation of the above-mentioned [15], wherein the drug is rivastigmine.

The present invention also relates to the following [17]-[30].

[17] An adhesive sheet for skin comprising a support and an adhesive layer formed on the support, wherein
the adhesive layer comprises
at least a thermoplastic elastomer, and
more than 120 parts by weight and not more than 800 parts by weight of non-volatile hydrocarbon oil and more than 3 parts by weight and not more than 500 parts by weight of polyisobutylene per 100 parts by weight of the elastomer,
the polyisobutylene is a mixture of a low molecular weight polyisobutylene having a viscosity average molecular weight of more than 30,000 and not more than 100,000, and a high molecular weight polyisobutylene having a viscosity average molecular weight of more than 500,000 and not more than 5,000,000, and
a tackifier is not contained.

[18] The adhesive sheet for skin of the above-mentioned [17], wherein the content of the polyisobutylene is more than 10 parts by weight and not more than 300 parts by weight, per 100 parts by weight of the thermoplastic elastomer.

[19] The adhesive sheet for skin of the above-mentioned [18], wherein the content of the polyisobutylene is more than 20 parts by weight and not more than 130 parts by weight, per 100 parts by weight of the thermoplastic elastomer.

[20] The adhesive sheet for skin of any one of the above-mentioned [17]-[19], wherein the low molecular weight polyisobutylene has a viscosity average molecular weight of more than 50,000 and not more than 100,000.

[21] The adhesive sheet for skin of any one of the above-mentioned [17]-[20], wherein the thermoplastic elastomer is a mixture of a triblock copolymer and a diblock copolymer, and a content of the diblock copolymer in the mixture is not less than 20 wt %.

[22] The adhesive sheet for skin of the above-mentioned [21], wherein the content of the diblock copolymer in the mixture is not less than 30 wt %.

[23] The sheet of any one of the above-mentioned [17]-[22], wherein the thermoplastic elastomer is a styrene-based block copolymer.

[24] The adhesive sheet for skin of the above-mentioned [23], wherein the styrene-based block copolymer is a mixture of a styrene-isoprene-styrene block copolymer and a styrene-isoprene block copolymer.

[25] The adhesive sheet for skin of any one of the above-mentioned [17]-[24], wherein a 25 wt % toluene solution of the thermoplastic elastomer has a solution viscosity at 25° C. of not less than 0.5 Pa·s.

[26] The adhesive sheet for skin of the above-mentioned [25], wherein the 25 wt % toluene solution of the thermoplastic elastomer has a solution viscosity at 25° C. of not less than 0.7 Pa·s.

[27] The adhesive sheet for skin of any one of the above-mentioned [17]-[26], wherein the non-volatile hydrocarbon oil has a kinematic viscosity at 40° C. of not less than 80 mm$^2$/s.

[28] The adhesive sheet for skin of any one of the above-mentioned [17]-[27], wherein the content of the non-volatile hydrocarbon oil in the adhesive layer is not less than 30 wt % and not more than 80 wt %.

[29] A percutaneous absorption preparation comprising the adhesive sheet for skin of any one of the above-mentioned [17]-[28], and a drug or a pharmaceutically acceptable salt thereof comprised in the adhesive layer of the adhesive sheet.

[30] The percutaneous absorption preparation of the above-mentioned [29], wherein the drug is rivastigmine.

Effect of the Invention

The adhesive sheet for skin of the present invention shows sufficient adhesiveness when attached to the skin, and causes low skin irritation.

Furthermore, the percutaneous absorption preparation of the present invention is excellent in the adhesiveness to the skin, low skin irritation, as well as drug releasability.

DESCRIPTION OF EMBODIMENTS

First, an adhesive sheet for skin and a percutaneous absorption preparation of the first embodiment of the present invention are explained.

The adhesive sheet for skin and percutaneous absorption preparation of the first embodiment of the present invention (hereinafter "adhesive sheet for skin and percutaneous absorption preparation" are sometimes to be referred to as "adhesive sheet for skin and the like" in the present specification) has an adhesive layer formed on a support, wherein the adhesive layer comprises a thermoplastic elastomer, non-volatile hydrocarbon oil and medium molecular weight polyisobutylene having a viscosity average molecular weight of more than 100,000 and not more than 500,000, and a tackifier is not contained.

The "thermoplastic elastomer" is an elastomer having thermoplasticity wherein it is softened when heat is added to show flowability, and returns to a rubbery elastic body by cooling, and various thermoplastic elastomers of urethane, acrylic, styrene, olefin and the like can be mentioned.

In the present invention, to impart sufficient skin adhesiveness to an adhesive sheet and a percutaneous absorption preparation, the thermoplastic elastomer is a mixture of a triblock copolymer and a diblock copolymer, and the content of the diblock copolymer in the mixture is preferably not less than 20 wt %, more preferably not less than 30 wt %. When the mixing ratio of the diblock copolymer is too low, skin adhesiveness tends to decrease. When it is too high, shape retention of the adhesive layer tends to be degraded, which in turn may cause inconveniences on attachment to the skin, such as adhesive residue on the skin after peeling off and the like. Therefore, the mixing ratio of the triblock copolymer and the diblock copolymer [(triblock copolymer)/(diblock copolymer)] is more preferably 20/80-75/25, further more preferably 30/70-70/30, in weight ratio.

Particularly, to improve balance of the adhesive properties of the obtained adhesive sheet for skin and the like (balance of adhesiveness to skin and skin irritation, and adhesive residue), a 25 wt % toluene solution of the thermoplastic elastomer preferably has a solution viscosity at 25° C. of not less than 0.5 Pa·s, further preferably not less than 0.7 Pa·s, particularly preferably not less than 0.9 Pa·s. While the upper limit of the solution viscosity is not particularly limited, it is preferably not more than 2.0 Pa·s, more preferably not more than 1.8 Pa·s.

As used herein, the "solution viscosity of 25 wt % toluene solution at 25° C." is a value measured based on "viscosity measurement method of styrene.isoprene.styrene block copolymer" described on page 375 of the Japanese Pharmaceutical Excipients 2003" (published by YAKUJI NIPPO LIMITED).

Particularly, styrene-based thermoplastic elastomer, especially styrene-based block copolymer, is preferably used as the thermoplastic elastomer to simultaneously achieve sufficient skin adhesiveness and low skin irritation, which is the object of the present invention. Specific examples of the styrene-based block copolymer include styrene-butadiene block copolymer, styrene-butadiene-styrene block copolymer, styrene-isoprene block copolymer, styrene-isoprene-styrene block copolymer, styrene-ethylene/butylene block copolymer, styrene-ethylene/butylene-styrene block copolymer, styrene-ethylene/propylene block copolymer, styrene-ethylene/propylene-styrene block copolymer, styrene-isobutylene block copolymer, styrene-isobutylene-styrene block copolymer and the like. In the above, "ethylene/butylene" shows an ethylene and butylene copolymer block, and "ethylene/propylene" shows an ethylene and propylene copolymer block. These styrene-based block copolymers can be preferably used in combination at the above-mentioned mixing ratio of the triblock copolymer and the diblock copolymer, and not less than 3 kinds may be used in combination. That is, one or more kinds of each of triblock copolymer and diblock copolymer can be used.

From the aspects of simultaneous achievement of sufficient skin adhesiveness and low skin irritation, and availability and handling property of the products for skin preparation, of the above-mentioned styrene-based block copolymers, a mixture containing a styrene-isoprene-styrene block copolymer and a styrene-isoprene block copolymer is preferably used. Particularly, a mixture of a styrene-isoprene-styrene block copolymer and a styrene-isoprene block copolymer is preferably used from the aspect of adhesiveness.

For the object of the present invention, a styrene-isoprene-styrene block copolymer preferably has a content of the styrene in the copolymer of 5 wt %-60 wt %, more preferably 10 wt %-50 wt %. In addition, it preferably has a weight average molecular weight as measured by gel permeation chromatography of not less than 20,000 and not more than 500,000, more preferably not less than 30,000 and not more than 300,000. As the styrene-isoprene block copolymer, one having a content of the styrene in the copolymer of not less than 5 wt % and not more than 50 wt %, more preferably not less than 10 wt % and not more than 40 wt %. In addition, it preferably has a weight average molecular weight as measured by gel permeation chromatography of not less than 10,000 and not more than 500,000, more preferably not less than 20,000 and not more than 300,000. The mixture of the styrene-isoprene-styrene block copolymer and the styrene-isoprene block copolymer preferably has a weight average molecular weight as measured by gel permeation chromatography of not less than 20,000 and not more than 500,000, more preferably not less than 30,000 and not more than 300,000.

As the styrene-isoprene-styrene block copolymer and the styrene-isoprene block copolymer, copolymers produced by a method known per se can be respectively used. As the styrene-isoprene-styrene block copolymer and the styrene-isoprene block copolymer, commercially available products that satisfy the above-mentioned properties can be respectively used. In addition, a mixture of the styrene-isoprene-styrene block copolymer and the styrene-isoprene block copolymer is also commercially available, and a commercially available product of a mixture of the styrene-isoprene-styrene block copolymer and the styrene-isoprene block copolymer at the above-mentioned mixing ratio, which satisfies the above-mentioned properties can be preferably used.

Examples of such commercially available product include "KRATON D1111", "KRATON D1163", "KRATON D1113" and "KRATON D1119" manufactured by KRATON POLYMERS, "JSR SIS5002", "JSR SIS5229", "JSR SIS5403" and "JSR SIS5505" manufactured by JSR Corporation, "Quintac 3421", "Quintac 3433N", "Quintac 3520", "Quintac 3450", "Quintac 3270" manufactured by Zeon Corporation and the like. Of these, from the aspects of the above-mentioned mixing ratio of triblock copolymer and diblock copolymer, and solution viscosity, "KRATON D1163", "KRATON D1113", "JSR SIS5403", "JSR SIS5505", "Quintac 3433N", "Quintac 3520" are preferably used, and "JSR SIS5505", "Quintac 3520" are particularly preferably used.

When the content of the thermoplastic elastomer in the adhesive layer is too small, the shape of the adhesive layer is difficult to maintain, and when it is too much, skin adhesiveness tends to be insufficient. Therefore, the content of the thermoplastic elastomer in the adhesive layer of the adhesive sheet for skin and the like of the present invention is preferably not less than 8 wt %, more preferably not less than 10 wt %, further preferably not less than 12 wt %, particularly preferably not less than 15 wt %. It is preferably not more than 44 wt %, more preferably not more than 42 wt %, further preferably not more than 40 wt %, particularly preferably not more than 35 wt %.

In a more specific and preferable embodiment, the content of the thermoplastic elastomer in the adhesive layer is 8 wt %-44 wt %, more preferably 8 wt %-42 wt %, particularly preferably 10 wt %-40 wt %.

In the adhesive sheet for skin and the like of the first embodiment of the present invention, the adhesive layer contains non-volatile hydrocarbon oil.

As the non-volatile hydrocarbon oil, a chain saturated hydrocarbon having about 20-40 carbon atoms or a chain unsaturated hydrocarbon having about 20-40 carbon atoms is preferable and, for example, liquid paraffin, squalene, squalane, pristane and the like can be mentioned. In view of easy availability, liquid paraffin is more preferable. Liquid paraffin is a mixture of colorless odorless liquid alkanes having not less than 20 carbon atoms. In the present invention, liquid paraffin compatible with the standard defined in the Japanese Pharmacopoeia, the United States Pharmacopeia and the like, and the like can be preferably used. The non-volatile hydrocarbon oil having high viscosity is preferable, and liquid paraffin having high viscosity is particularly preferably used from the aspect of adhesiveness.

To be specific, the non-volatile hydrocarbon oil preferably shows kinematic viscosity at 40° C. of not less than 60 mm$^2$/s, more preferably not less than 70 mm$^2$/s, further more preferably not less than 80 mm$^2$/s, particularly preferably not less than 100 mm$^2$/s. While the upper limit of the kinematic viscosity is not particularly limited, it is preferably not more than 500 mm$^2$/s, more preferably not more than 300 mm$^2$/s, for example, from the aspects of easy handling, easy availability and the like.

As used herein, the "kinematic viscosity" is a value obtained by converting the viscosity (mPa·s) measured according to "the Japanese Pharmacopoeia 16th Edition", General Test Method "2.53 viscosity measurement method", "Second method rotary viscosimeter method (2.12 single cylinder type rotary viscosimeter (Brookfield viscosimeter)" (page 59) to the kinematic viscosity.

The adhesive sheet for skin and the like of the first embodiment of the present invention contain the above-mentioned non-volatile hydrocarbon oil at a weight ratio of more than 120 parts by weight and not more than 800 parts by weight, relative to 100 parts by weight of the thermoplastic elastomer. When the content of the non-volatile hydrocarbon oil relative to 100 parts by weight of the thermoplastic elastomer is more than 800 parts by weight, shape retention of the adhesive layer tends to be difficult. On the other hand, when the content of the non-volatile hydrocarbon oil is not more than 120 parts by weight, the adhesive becomes too hard and sufficient skin adhesiveness tends to be unachieved. Particularly, the followability to the moving skin during adhesion becomes poor, thus resulting in possible falling off during adhesion. From such aspect, the content of the non-volatile hydrocarbon oil in the adhesive layer is more preferably 121 parts by weight-800 parts by weight, further preferably 130 parts by weight-600 parts by weight, particularly preferably 150 parts by weight-500 parts by weight, relative to 100 parts by weight of the thermoplastic elastomer.

Even within this range, when a non-volatile hydrocarbon oil having a low kinematic viscosity, for example, one having a kinematic viscosity at 40° C. of less than 80 mm$^2$/s, is used relative to a thermoplastic elastomer whose 25 wt % toluene solution shows a low solution viscosity at 25° C., particularly less than 0.5 Pa·s, protrusion of the adhesive is observed during preservation and adhesion, and inconveniences such as attachment to packing materials and clothes tend to occur when the content of the non-volatile hydrocarbon oil is high.

In such case, therefore, the content of the non-volatile hydrocarbon oil in the adhesive layer is preferably 121 parts by weight-300 parts by weight, more preferably 130 parts by weight-250 parts by weight, particularly preferably 130 parts by weight-200 parts by weight, relative to 100 parts by weight of the thermoplastic elastomer.

The content of the non-volatile hydrocarbon oil in the adhesive layer is preferably not less than 17 wt %, further preferably not less than 25 wt %, further preferably not less than 35 wt %, particularly preferably not less than 45 wt %. In addition, it is preferably not more than 88 wt %, more preferably not more than 85 wt %, further preferably not more than 80 wt %, particularly preferably not more than 70 wt %.

In the present invention, "polyisobutylene" contained in the adhesive layer is a polymer of isobutylene, which is an elastic rubbery semisolid or viscous substance, and added to impart sufficient skin adhesiveness to an adhesive sheet for skin and the like.

In the first embodiment of the present invention, a medium molecular weight polyisobutylene having a viscosity average molecular weight of more than 100,000 and not more than 500,000 is used. When a low molecular weight polyisobutylene having a viscosity average molecular weight of not more than 100,000 is singly added, the obtained adhesive layer may produce inconveniences such as an adhesive residue on detachment after attachment and the like. On the other hand, even when a high molecular weight polyisobutylene having a viscosity average molecular weight of more than 500,000 is singly added, a skin adhesiveness improving effect is not afforded. A high molecular weight polyisobutylene has low solubility in solvent, is difficult to melt by heating, and is not easy to use. In the present invention, it is preferable to use a medium molecular weight polyisobutylene singly to afford well-balanced low skin irritation and high skin adhesiveness. When higher adhesiveness is desired, a low molecular weight polyisobutylene can also be mixed and used concurrently, and when adhesive residue, stickiness and skin irritation are to be suppressed more, a high molecular weight polyisobutylene can also be mixed and used concurrently.

The viscosity average molecular weight of polyisobutylene can be determined from the viscosity measured using Ubbelohde viscometer and the like and by the Schulz-Blaschke equation and the Mark-Howink-Sakurada equation.

As polyisobutylene, an isobutylene polymer produced by a method known per se can be used. Particularly, in an adhesive layer of the present invention which is for attachment to skin, those compatible with the standard defined in the Japanese Pharmaceutical Excipients, the United States Pharmacopeia and the like, and the like can be preferably used. As polyisobutylene, commercially available products each meeting the above-mentioned viscosity average molecular weight can be used.

Examples of the commercially available medium molecular weight polyisobutylene include "Oppanol B30SF", "Oppanol B50SF", "Oppanol B50" manufactured by BASF and the like. Examples of the low molecular weight polyisobutylene sometimes used in combination with medium molecular weight polyisobutylene include "Oppanol B10SFN", "Oppanol B10N", "Oppanol B12SFN", "Oppanol B15SFN", "Oppanol B15N" manufactured by BASF and the like, and examples of the high molecular weight polyisobutylene include "Oppanol B80", "Oppanol B100", "Oppanol B150", "Oppanol B200" manufactured by BASF and the like. From the aspects of solubility in solvent when producing a coating solution, balance of adhesive properties of the obtained adhesive sheet for skin and the like (balance of adhesiveness to skin and skin irritation, adhesive residue), among the above-mentioned medium molecular weight polyisobutylenes, "Oppanol B50SF", "Oppanol B50" are used particularly preferably.

When the content of polyisobutylene in the adhesive layer is too small, skin adhesiveness becomes insufficient. When the content is too high, skin adhesiveness becomes too strong to cause skin irritation, and adhesive residue and the like on detachment sometimes pose problems. Therefore, the content of polyisobutylene in the adhesive layer of the adhesive sheet for skin of the present invention and the like is preferably more than 3 parts by weight, more preferably more than 10 parts by weight, further preferably more than 20 parts by weight, further more preferably more than 30 parts by weight, per 100 parts by weight of the thermoplastic elastomer. Also, it is preferably not more than 500 parts by weight, more preferably not more than 300 parts by weight, further preferably not more than 200 parts by weight, further more preferably not more than 130 parts by weight, particularly preferably not more than 100 parts by weight, per 100 parts by weight of the thermoplastic elastomer.

In a more specific and preferable embodiment, the content of polyisobutylene in the adhesive layer is 0.3 wt %-69 wt %, more preferably 1 wt %-50 wt %, still more preferably 2 wt %-40 wt %, further preferably 3 wt %-30 wt %, particularly preferably 5 wt %-25 wt %.

In the adhesive sheet for skin and the like of the first embodiment of the present invention, good skin adhesiveness can be exhibited without using a tackifier capable of causing skin irritation but by containing a thermoplastic elastomer, non-volatile hydrocarbon oil, and medium molecular weight polyisobutylene having a viscosity average molecular weight of more than 100,000 and not more than 500,000 at the above-mentioned contents and content ratios in the adhesive layer.

Here, the tackifier is a resin generally used widely to impart skin adhesiveness in the field of a preparation for attachment to skin, and examples thereof include rosin resin, polyterpene resin, coumarone-indene resin, petroleum resin, terpene-phenol resin, alicyclic saturated hydrocarbon resin and the like. These are not used in the present invention.

An adhesive sheet for skin and a percutaneous absorption preparation of the second embodiment of the present invention are explained below.

The adhesive sheet for skin and the like of the second embodiment of the present invention have a support and an adhesive layer formed on the support, wherein the adhesive layer comprises a thermoplastic elastomer, more than 120 parts by weight and not more than 800 parts by weight of non-volatile hydrocarbon oil and more than 3 parts by weight and not more than 500 parts by weight of polyisobutylene per 100 parts by weight of the elastomer, the polyisobutylene is a mixture of a low molecular weight polyisobutylene having a viscosity average molecular weight of more than 30,000 and not more than 100,000, and a high molecular weight polyisobutylene having a viscosity average molecular weight of more than 500,000 and not more than 5,000,000, and a tackifier is not contained.

The "thermoplastic elastomer" used in the adhesive sheet for skin and the like of the second embodiment and the content thereof in the adhesive layer are the same as those in the adhesive sheet for skin and the like of the above-mentioned the first embodiment.

The adhesive sheet for skin and the like of the second embodiment of the present invention also contains non-volatile hydrocarbon oil in the adhesive layer.

The detail of the non-volatile hydrocarbon oil is the same as that of the adhesive sheet for skin and the like of the above-mentioned first embodiment.

The adhesive sheet for skin and the like of the second embodiment contains the non-volatile hydrocarbon oil in the adhesive layer at a weight ratio of more than 120 parts by weight and not more than 800 parts by weight, relative to 100 parts by weight of the thermoplastic elastomer. When the content of the non-volatile hydrocarbon oil relative to 100 parts by weight of the thermoplastic elastomer is more than 800 parts by weight, shape retention of the adhesive layer becomes difficult. On the other hand, when the content of the non-volatile hydrocarbon oil is not more than 120 parts by weight, the adhesive layer becomes too hard and sufficient skin adhesiveness tends to be unachieved. Particularly, the followability to the moving skin during adhesion becomes poor, thus resulting in possible falling off during adhesion. From such aspect, the content of the non-volatile hydrocarbon oil in the adhesive layer is preferably 121 parts by weight-800 parts by weight, further preferably 130 parts by weight-600 parts by weight, particularly preferably 150 parts by weight 500 parts by weight, relative to 100 parts by weight of the thermoplastic elastomer.

Even within this range, when a non-volatile hydrocarbon oil having a low kinematic viscosity, for example, one having a kinematic viscosity at 40° C. of less than 80 mm$^2$/s, is used relative to a thermoplastic elastomer whose 25 wt % toluene solution shows a low solution viscosity at 25° C., particularly less than 0.5 Pa·s, protrusion of the adhesive is observed during preservation and adhesion, and inconveniences such as attachment to packing materials and clothes tend to occur when the content of the non-volatile hydrocarbon oil is high.

In such case, therefore, the content of the non-volatile hydrocarbon oil in the adhesive layer is preferably 121 parts by weight-300 parts by weight, further preferably 130 parts by weight-250 parts by weight, particularly preferably 130 parts by weight-200 parts by weight, relative to 100 parts by weight of the thermoplastic elastomer.

The content of the non-volatile hydrocarbon oil in the adhesive layer is preferably not less than 17 wt %, more preferably not less than 25 wt %, further preferably not less than 35 wt %, particularly preferably not less than 45 wt %. In addition, it is preferably not more than 88 wt %, more preferably not more than 85 wt %, further preferably not more than 80 wt %, particularly preferably not more than 70 wt %.

To take balance of the low skin irritation and high skin adhesiveness, which is the object of the present invention, a mixture of a low molecular weight polyisobutylene having a viscosity average molecular weight of more than 30,000 and not more than 100,000, and a high molecular weight polyisobutylene having a viscosity average molecular weight of more than 500,000 and not more than 5,000,000 is used as the polyisobutylene.

The viscosity average molecular weight of polyisobutylene can be determined from the viscosity measured using Ubbelohde viscometer and the like and by the Schulz-Blaschke equation and the Mark-Howink-Sakurada equation.

As polyisobutylene, an isobutylene polymer produced by a method known per se can be used. Particularly, in an adhesive layer of the adhesive sheet for skin and the like of the present invention, those compatible with the standard defined in the Japanese Pharmaceutical Excipients, the United States Pharmacopeia and the like, and the like can be preferably used. As polyisobutylene, commercially available products each meeting the above-mentioned viscosity average molecular weight can be used.

Examples of such commercially available product as low molecular weight polyisobutylene include "Oppanol B10SFN", "Oppanol B10N", "Oppanol B12SFN", "Oppanol B15SFN", "Oppanol B15N" manufactured by BASF and the like, and examples of the high molecular weight polyisobutylene include "Oppanol B80", "Oppanol B100", "Oppanol B150", "Oppanol B200" manufactured by BASF and the like. Of these, from the aspects of solubility when producing a coating solution, balance of adhesive properties of the obtained adhesive sheet for skin and the like (balance of adhesiveness to skin and skin irritation, adhesive residue), "Oppanol B15SFN" and "Oppanol B15N" having a viscosity average molecular weight of 50,000-100,000 are particularly preferably used as low molecular weight polyisobutylene, and "Oppanol B80" is particularly preferably used as high molecular weight polyisobutylene.

When the content of polyisobutylene in the adhesive layer is too small, skin adhesiveness becomes insufficient. When the content is too high, skin adhesiveness becomes too strong to cause skin irritation, and adhesive residue and the like on detachment sometimes pose problems. Therefore, the content of polyisobutylene in the adhesive layer and the like of the adhesive sheet for skin in this embodiment is more than 3 parts by weight, preferably more than 10 parts by weight, more preferably more than 20 parts by weight, more preferably more than 30 parts by weight, per 100 parts by weight of the thermoplastic elastomer. Also, it is not more than 500 parts by weight, preferably not more than 300 parts by weight, more preferably not more than 200 parts by weight, further preferably not more than 130 parts by weight, per 100 parts by weight of the thermoplastic elastomer.

To suppress skin irritation and adhesive residue while improving skin adhesiveness, the content weight ratio of low molecular weight polyisobutylene and high molecular weight polyisobutylene (low molecular weight polyisobutylene/high molecular weight polyisobutylene) is preferably set to 90/10-45/55, further preferably 80/20-50/50, particularly preferably 75/25-60/40.

In a more specific and preferable embodiment, the content of polyisobutylene in the adhesive layer is 0.3 wt %-69 wt %, more preferably 1 wt %-50 wt %, still more preferably 2 wt %-40 wt %, further preferably 3 wt %-30 wt %, particularly preferably 5 wt %-25 wt %.

In the adhesive sheet for skin and the like of this embodiment, good skin adhesiveness can be exhibited without using a tackifier capable of causing skin irritation but by containing a thermoplastic elastomer, non-volatile hydrocarbon oil and low molecular weight polyisobutylene and high molecular weight polyisobutylene at the above-mentioned contents and content ratios in the adhesive layer.

Therefore, also in the adhesive sheet for skin and the like of this embodiment, a tackifier is not used as in the above-mentioned first embodiment.

In the present invention, a drug or a pharmaceutically acceptable salt thereof is further contained in the adhesive layer of the adhesive sheets for skin of the above-mentioned first embodiment and second embodiment, whereby a percutaneous absorption preparation can be obtained.

The "drug or a pharmaceutically acceptable salt thereof" in the present invention refers to a drug or a pharmaceutically acceptable salt thereof to be percutaneously absorbed, and is not particularly limited. Examples of the drug include anti-inflammatory agents such as acetaminophen, phenacetin, mefenamic acid, diclofenac sodium, flufenamic acid, aspirin, sodium salicylate, methyl salicylate, salicyl acid glycol, aminopyrine, alclofenac, ibuprofen, naproxen, flurbiprofen, ketoprofen, amfenac sodium, mepirizole, indomethacin, piroxicam, felbinac and the like; steroidal anti-inflammatory agents such as hydrocortisone, triamcinolone, dexamethasone, prednisolone and the like; vasodilators such as diltiazem hydrochloride, pentaerythritol tetranitrate, isosorbide nitrate, tradipil, nicorandil, nitroglycerol, prenylamine lactate, molsidomine, aluminum nitrite, tolazoline hydrochloride, nifedipine and the like; antiarrhythmic agents such as procaineamide hydrochloride, lidocain hydrochloride, propranolol hydrochloride, alprenolol hydrochloride, atenolol, nadolol, metoprolol tartrate, ajmaline, disopyramide, mexiletine hydrochloride and the like; antihypertensive agents such as ecarazine hydrochloride, indapamide, clonidine hydrochloride, bunitrolol hydrochloride, labetalol hydrochloride, captopril, guanabenz acetate, mebutamate, bethanidine sulfate and the like; antitussive expectorants such as carbetapentane citrate, cloperastine, oxeladin tannate, cloputinol hydrochloride, clofedanol hydrochloride, noscapine hydrochloride, ephedrine hydrochloride, isoproterenol hydrochloride, cloriprenaline hydrochloride, methoxyphenamine hydrochloride, procaterol hydrochloride, tulobuterol hydrochloride, clenputerol hydrochloride, ketotifen fumarate and the like; antineoplastics such as cyclophosphamide, fluorouracil, degafur, mitomycin C, procarbazine hydrochloride, doxifluridine, ranimustine and the like; topical anesthetics such as ethyl aminobenzoate, tetracaine hydrochloride, procaine hydrochloride, dibucaine hydrochloride, oxybuprocaine hydrochloride, propitocaine hydrochloride and the like; hormone drugs such as propylthiouracil, thiamazole, metelonone acetate, estradiol, estriol, progesterone and the like; antihistamine agents such as diphenhydramine hydrochloride, chlorpheniramine maleate, promethazine, dyproheptadine hydrochloride, diphenylpyraline hydrochloride and the like; anticoagulants such as warfarin potassium, ticlopidine hydrochloride and the like; antispasmodics such as atropine methylbromide, scopolamine and the like; general anesthetics such as thiopental sodium, pentobarbital sodium and the like; hypnotics or analgesics such as bromovalerylurea, amobarbital, phenobarbital and the like; antiepileptic agents such as phenytoin sodium and the like; analeptics or stimulant drugs such as methamphetamine hydrochloride and the like; antidizziness drugs such as difendol hydrochloride, betahistine mesylate and the like; drugs for psycho neurosis such as chlorpromazine hydrochloride, thioridazine, meprobamate, imipramine hydrochloride, chlordiazepoxide, diazepam, risperidone, paliperidone, olanzapine, aripiprazole, paroxetine, duloxetine and the like; skeletal muscle relaxants such as suxamethonium hydrochloride, eperisone hydrochloride and the like; drugs for autonomic nerve such as neostigmine bromide, bethanechol chloride and the like; antiparkinsonian drugs such as amantadine hydrochloride, rotigotine, ropinirole and the like; anti-Alzheimer-type dementia drugs such as donepezil, galanthamine, memantine, rivastigmine and the like; diuretics such as hydroflumethiazide, isosorbide, furosemide and the like; vasoconstrictors such as phenylephrine hydrochloride and the like; respiratory stimulants such as lobeline bromide, dimorpholamine, naloxone hydrochloride and the like; peptic ulcer therapeutic agents such as glycopyrronium bromide, proglumide, cetraxate hydrochloride, cimetidine, spizofurone and the like; cholagogues such as ursodesoxycholic acid, osalmid and the like; drugs for urogenital system and anus such as hexamine, sparteine, dinoprost, ritodrine hydrochloride, oxybutynin, tolterodine, solifenacin, darifenacin and the like; drugs for parasitic skin disease such as salicylic acid, ciclopiroxolamine, coroconazole hydrochloride and the like; skin softeners such as urea and the like; vitamins such as calcitriol, thiamine hydrochloride, riboflavin sodium phosphate, pyridoxine hydrochloride, nicotinamide, panthenol, ascorbic acid and the like; mineral preparations such as calcium chloride, potassium iodide, sodium iodide and the like; hemostatics such as ethamsylate and the like; drugs for liver disease such as tiopronin and the like; drugs for habitual intoxication such as cyanamide and the like; therapeutic agents for gout such as colchicine, probenecid, sulfinpyrazone and the like; drugs for diabetes such as tolbutamide, chlorpropamide, glymidinesodium, glypuzole, puformin hydrochloride, insulin and the like; antibiotics such as benzylpenicillin potassium, propicillin potassium, cloxacillin sodium, ampicillin sodium, bacampillicin hydrochloride, carbenicillin sodium, cephaloridine, cefoxitin sodium, erythromycin, chloramphenicol, tetracycline, kanamycin sulfate, cycloserine and the like; chemotherapeutic agents such as isocyanide, pyrazinamide, ethionamide and the like; narcotics such as morphine hydrochloride, codeine phosphate, cocaine hydrochloride, pethidine hydrochloride, fentanyl citrate and the like, and the like. As pharmaceutically acceptable salts of these drugs, not only the above-mentioned salts but also various salts can be used, and the drugs in a free form can also be used.

In the adhesive sheet for skin and the like of the first embodiment and the second embodiment of the present invention, an adhesive layer having the above-mentioned constitution can be formed flat on a support.

In the present invention, the "support" is not particularly limited, and one widely used for an adhesive sheet for skin and the like can be used. For example, stretchable or nonstretchable woven fabric or nonwoven fabric of polyethylene, polypropylene, poly(ethylene terephthalate) and the like, films of polyesters such as poly(ethylene terephthalate) and the like, polyolefins such as polyethylene, polypropylene and the like, polyurethane, ethylenevinyl acetate copolymer, polyvinyl chloride and the like, or a foamed support of polyolefin, polyurethane and the like can be mentioned. These may be used alone, or a laminate of plural kinds thereof may be used.

Furthermore, to prevent accumulation of static electricity on the support, the aforementioned woven fabric, nonwoven fabric, film and the like constituting the support may contain an antistatic agent. Moreover, to achieve good anchor property to the adhesive layer, a nonwoven fabric or woven fabric, or a laminate thereof with a film can be used as a support. The thickness of a film as the support is generally 10-100 μm, preferably 15-50 μm, and the thickness of woven fabric, nonwoven fabric, and a porous sheets such as foamed support and the like is generally 50-2,000 μm, preferably 100-1,000 μm.

The adhesive sheet for skin and the like of the first embodiment and the second embodiment of the present invention can also be provided with a release liner generally used in this field. As the release liner, glassine, resin films of polyolefins such as polyethylene, polypropylene and the like, polyesters such as poly(ethylene terephthalate) and the like, polystyrene and the like, aluminum film, foamed polyethylene film or foamed polypropylene film and the like, or a laminate of two or more kinds of those mentioned above can be used, which may be subjected to silicone treatment or fluorine resin treatment, embossing, hydrophilic processing, hydrophobic processing and the like, and the like can also be used. The thickness of the release liner is generally 10 μm-200 μm, preferably 15 μm-150 μm.

The adhesive sheet for skin and the like of the first embodiment and the second embodiment of the present invention can be produced by, for example, dissolving or dispersing a thermoplastic elastomer, polyisobutylene and non-volatile hydrocarbon oil, or a drug or a pharmaceutically acceptable salt thereof respectively in a solvent such as toluene and the like, preparing a coating solution for forming an adhesive layer, applying the obtained coating solution on a support, and then drying same. When a release liner is used, it can be laminated by pressing a release liner on an adhesive layer. Alternatively, the aforementioned coating solution may be applied on a release liner, dried to form an adhesive layer on a surface of the release liner, and thereafter the support may be press adhered on the adhesive layer.

As the solvent to be used for the coating solution, one capable of uniformly dissolving or dispersing thermoplastic elastomer, polyisobutylene, non-volatile hydrocarbon oil and drug or a salt thereof is preferable, and examples thereof include aromatic hydrocarbons such as toluene and the like, alicyclic hydrocarbons such as cyclohexane, methylcyclohexane and the like, aliphatic hydrocarbons such as hexane, heptane and the like, ethers such as tetrahydrofuran, diethyl ether, t-butyl methyl ether and the like, ketones such as acetone, methylethyl ketone, methyl isobutyl ketone and the like, alcohols such as ethanol, propanol, butanol and the like, acetates such as ethyl acetate, propyl acetate, isopropyl acetate, butyl acetate, isobutyl acetate and the like, and the like.

These solvents can be used alone, or two or more kinds thereof may be used in combination. In view of good solubility of each component constituting the adhesive layer, aromatic hydrocarbons such as toluene and the like, alicyclic hydrocarbons such as cyclohexane, methylcyclohexane and the like, aliphatic hydrocarbons such as hexane, heptane and the like may be used alone or in a mixture, and it is more preferable to use aromatic hydrocarbons such as toluene and the like, aliphatic hydrocarbons such as hexane, heptane and the like in combination with acetates such as ethyl acetate, propyl acetate, isopropyl acetate, butyl acetate, isobutyl acetate and the like. Moreover, since the balance of the solubility of thermoplastic elastomer and polyisobutylene is good, it is particularly preferable to use toluene alone, or aliphatic hydrocarbons such as hexane, heptane and the like in combination with acetates such as ethyl acetate, propyl acetate, isopropyl acetate, butyl acetate, isobutyl acetate and the like. Furthermore, to suppress generation of bubbles in drying, it is most preferable to use toluene, a mixed solvent of heptane and propyl acetate, and a mixed solvent of hexane and ethyl acetate. When the above-mentioned solvents are used in combination, the solubility of each component constituting the adhesive layer can be changed by the ratio thereof. For example, when a mixed solvent of aliphatic hydrocarbon and acetate is used, the mixing ratio thereof (aliphatic hydrocarbon/acetate) is preferably 10/90-80/20, further preferably 20/80-70/30, in weight ratio. It is particularly preferably 30/70-60/40, because dispersion of polyisobutylene in an adhesive sheet for skin and the like obtained after drying is good, skin adhesiveness is improved, and problems such as adhesive residue and the like upon detachment do not occur.

A coating solution forming an adhesive layer can be applied using, for example, a conventionally-used coater such as roll coater, die coater, gravure roll coater, reverse roll coater, kiss-roll coater, dip roll coater, bar coater, knife coater, spray coater and the like. In addition, the aforementioned coating solution is preferably dried under heating at, for example, about 40° C.-150° C., and the drying temperature, drying time and drying method can be adjusted according to the solvent to be used and the amount of use thereof.

The weight per unit area of the adhesive layer after drying may be adjusted according to the required skin adhesiveness and percutaneous absorbability. As the range affording skin adhesiveness and enabling production, the weight of the adhesive layer after drying is preferably 10 g/m$^2$-1,000 g/m$^2$, more preferably 20 g/m$^2$-800 g/m$^2$, further preferably 30 g/m$^2$-600 g/m$^2$.

In addition, the adhesive sheet for skin and the like of the first embodiment and the second embodiment of the present invention may contain excipient, antioxidant, flavor, colorant and the like as optional components.

Examples of the excipient include silicic acid compounds such as silicic anhydride, light anhydrous silicic acid, silicic hydride and the like; cellulose derivatives such as ethylcellulose, methylcellulose, hydroxypropylcellulose, hydroxypropylmethylcellulose and the like; water-soluble polymers such as poly(vinyl alcohol) and the like; aluminum compounds such as dried aluminum hydroxide gel, hydrous aluminum silicate and the like; kaolin, titanium oxide and the like.

Examples of the antioxidant include dibutylhydroxy-toluene, ascorbic acid, tocopherol, tocopherol ester derivative, butylhydroxyanisole, 2-mercaptobenzimidazole and the like.

Examples of the flavor include dl-camphor, dl-borneol, l-menthol and the like.

Examples of the colorants to be used in the present invention include red ferric oxide, yellow iron oxide, black iron oxide, Food Color Red No. 2, photosensitizer 201 and the like.

EXAMPLES

The present invention is explained in more detail in the following by referring to Examples and Comparative Examples, which are not to be construed as limitative.

Example of the first embodiment of the present invention is shown below.

[Examples 1-6, Comparative Examples 1-3]
Preparation of Adhesive Sheet for Skin

According to the formulation shown in Table 1, each component constituting the adhesive layer was measured. The constituent components of the adhesive layer are as follows.
(1) thermoplastic elastomer: styrene-isoprene-styrene block copolymer (SIS)/styrene-isoprene block copolymer (SI) mixture
(a) KRAYTON D1111 (in Table 1, abbreviated as "D111"); manufactured by Kraton Polymers, SIS/SI ratio (weight ratio)=85/15, solution viscosity of 25 wt % toluene solution at 25° C.=1.2 Pa·s
(b) KRAYTON D1119 (in Table 1, abbreviated as "D119"); manufactured by Kraton Polymers, SIS/SI ratio (weight ratio)=34/66, solution viscosity of 25 wt % toluene solution at 25° C.=0.34 Pa·s
(c) Quintac3520 (in Table 1, abbreviated as "QTC3520"); manufactured by Zeon Corporation, SIS/SI ratio (weight ratio)=22/78, solution viscosity of 25 wt % toluene solution at 25° C.=1.1 Pa·s
(d) JSR SIS5505 (in Table 1, abbreviated as "5505"); manufactured by JSR Corporation, SIS/SI ratio (weight ratio)=50/50, solution viscosity of 25 wt % toluene solution at 25° C.=1.05 Pa·s
(2) polyisobutylene
(a) low molecular weight polyisobutylene: Oppanol B10SFN (in Table 1, abbreviated as "B10SFN"); manufactured by BASF, viscosity average molecular weight=40,000
(b) medium molecular weight polyisobutylene: Oppanol B50SF (in Table 1, abbreviated as "B50SF"); manufactured by BASF, viscosity average molecular weight=400,000
(3) non-volatile hydrocarbon oil: liquid paraffin
(a) KAYDOL; manufactured by Fujichem Sonneborn, kinematic viscosity at 40° C.=67 mm$^2$/s
(b) Hydrobrite HV; manufactured by Fujichem Sonneborn, kinematic viscosity at 40° C.=247 mm$^2$/s First, polyisobutylene was dissolved in 70 parts by weight of toluene relative to 100 parts by weight of the total amount of a thermoplastic elastomer, polyisobutylene and liquid paraffin. In the aforementioned solution was further dissolved the thermoplastic elastomer, liquid paraffin was added and the mixture was stirred to give a coating solution for forming an adhesive layer.

The above-mentioned coating solution was applied to a silicone-treated poly(ethylene terephthalate) (PET) film (release liner) such that the thickness of the adhesive layer after drying was about 400 μm. After drying in an oven at 100° C. for 40 min, a PET film (support) was laminated on a surface of the adhesive layer, which was cut in the size of 15 cm×30 cm to give the object adhesive sheet for skin.

TABLE 1

| component | | | | | Ex. 1 | Ex. 2 | Ex. 3 | Ex. 4 | Ex. 5 | Ex. 6 | Com. Ex. 1 | Com. Ex. 2 | Com. Ex. 3 |
|---|---|---|---|---|---|---|---|---|---|---|---|---|---|
| thermo- plastic elastomer | styrene- isoprene- styrene block copolymer (SIS)/styrene- isoprene block copolymer (SI) mixture | product name | SIS/SI ratio | solution viscosity (Pa · s) | | | | | | | | | |
| | | D1111 | 85/15 | 1.2 | | | | | | | 40 | 40 | |
| | | D1119 | 34/66 | 0.34 | | | | | | | | 10 | 9 |
| | | QTC3520 | 22/78 | 1.1 | | | | | | 21 | | | |
| | | 5505 | 50/50 | 1.05 | 31 | 25 | 21 | 20 | | | | | |

TABLE 1-continued

| component | | | Ex. 1 | Ex. 2 | Ex. 3 | Ex. 4 | Ex. 5 | Ex. 6 | Com. Ex. 1 | Com. Ex. 2 | Com. Ex. 3 |
|---|---|---|---|---|---|---|---|---|---|---|---|
| polyiso-butylene | | product name / viscosity average molecular weight | | | | | | | | | |
| | low molecular weight | B10SFN / 40,000 | | | | | | | | 60 | 10 |
| | medium molecular weight | B50SF / 400,000 | 16 | 7 | 16 | 20 | 16 | 15 | | | |
| polyisobutylene content (parts by weight/thermoplastic elastomer 100 parts by weight) | | | 52 | 28 | 76 | 100 | 76 | 38 | 0 | 600 | 111 |
| non-volatile hydrocarbon oil | liquid paraffin | product name / viscosity*[2] (mm²/s) | | | | | | | | | |
| | | KAYDOL / 67 | | | | | | 45 | 60 | 30 | 81 |
| | | Hydrobrite HV / 247 | 53 | 68 | 63 | 60 | 63 | | | | |
| non-volatile hydrocarbon oil content (parts by weight/thermoplastic elastomer 100 parts by weight) | | | 171 | 272 | 300 | 300 | 300 | 113 | 150 | 300 | 900 |

*1; Unless particularly indicated, the values in Table show contents (wt %) in adhesive layer.
*[2] measured at 40° C.

[Comparative Example 4] Preparation of Silicone-Based Adhesive Sheet for Skin

According to the method described in [Example] of WO 2007/064407, a coating solution was prepared such that the composition after drying was the following composition, applied to a Teflon-treated poly(ethylene terephthalate) (PET) film (release liner) such that the weight per unit area after drying was 90 g/m², and dried.

A PET film (support) was laminated on a surface of the adhesive layer, which was cut in the size of 15 cm×30 cm to give the object adhesive sheet for skin.

<Coating Solution Composition>

| silicone-based adhesive ("Bio-PSA Q7-4301", manufactured by Dow Corning Corporation) | 98.9 (wt %) |
|---|---|
| silicone oil | 1.0 |
| vitamin E | 0.1 |

[Experimental Example 1] Adhesive Property Test (1) Preparation of Sample

The adhesive sheets for skin of Examples 1-6 and Comparative Examples 1-4 were each cut in the size of 25 mm×100 mm and used as samples.

(2) Peel Strength to Stainless Steel (SUS)

According to Japanese Industrial Standard (JIS) Z0237: 2009, each sample was attached to a stainless steel (SUS304) plate, and the stress when peeled in the 180° direction at a rate of 300 mm/min was measured using motorized test stand MX2-500N and digital force gauge ZP-50N manufactured by IMADA.

(3) Peel Strength to Human

According to JIS Z0237:2009, each sample was attached to a normal volunteer on the inside of forearm, and the stress when peeled in the 90° direction at a rate of 300 mm/min was measured using motorized test stand MX2-500N and digital force gauge ZP-50N manufactured by IMADA.

In addition, the pain felt when the sample was peeled was evaluated according to the following criteria <Evaluation Criteria>
0: pain is scarcely felt
1: slight pain is felt
2: considerable pain is felt

[Experimental Example 2] Primary Skin Irritation Test

The adhesive sheets for skin of Examples 1-6 and Comparative Examples 1-4 were each cut in the size of 2.5 cm square and used as samples.

Three days before the start of attachment, dorsal hair of kbs: JW female domestic rabbit (17-week-old) was shaven with an electric clipper, and each sample was attached to the skin (each n=3). Oil paper was placed thereon to cover the attached site, an underlap tape (manufactured by Nichiban Co., Ltd.) was wound from the chest to the whole abdomen, and a jacket for domestic rabbit (BJ03, manufactured by Bioresearch Center Co., Ltd.) was set thereon. After fixing for 24 hr, the sample was removed, and the level of skin irritation response was evaluated based on the method described in J. Pharmacol. Exp. Ther. 82, 377-390 (1944) for 1 hr, for 24 hr, for 48 hr and for 72 hr after the removal.

That is, after sample removal, after elapse of each of the above-mentioned times, erythema and eschar formation and edema formation were evaluated according to the following evaluation criteria, and scored. An average of respective evaluation points was determined, the primary evaluation value was calculated, and an average of the average evaluation value after elapse of each of the above-mentioned times was determined for each domestic rabbit and taken as a primary irritation index (P.I.I.). The P.I.I. value was 0 at the lowest and 8 at the highest, and the values are divided into 4 categories of primary skin irritation response shown in Table 2.

<Evaluation Criteria of Skin Irritation Response>
[Formation of Erythema and Eschar]
no erythema; 0 point
very slight (barely perceptible level of) erythema; 1 point
well-defined erythema; 2 points
moderate to severe erythema; 3 points
severe erythema to eschar formation of level preventing erythema scoring; 4 points

[Formation of Edema]
  no edema; 0 point
  very slight (barely perceptible level of) edema; 1 point
  slight edema (edges of area well defined by definite rising); 2 points
  moderate edema (raised approximately 1 mm); 3 points
  severe edema (raised more than 1 mm and extending beyond exposure area); 4 points

TABLE 2

| category of primary skin irritation response | P.I.I. |
|---|---|
| no irritation | 0-0.4 |
| weak irritation | 0.5-1.9 |
| moderate irritation | 2-4.9 |
| strong irritation | 5-8 |

The results of the above-mentioned test are collectively shown in Table 3.

The adhesive sheets for skin of Comparative Examples 2, 3 failed to stably maintain the adhesive layer, and the above-mentioned test could not be performed.

TABLE 3

| | | Ex. 1 | Ex. 2 | Ex. 3 | Ex. 4 | Ex. 5 | Ex. 6 | Com. Ex. 1 | Com. Ex. 4 silicone-based |
|---|---|---|---|---|---|---|---|---|---|
| adhesive property | peel strength to SUS (N/25 mm) | 2.7 | 1.2 | 2.5 | 3.2 | 10.8 | 1.0 | 0.1 | 16.8 |
| | peeled state to SUS — adhesive residue | none | none | ultra-thin | none | delami | none | none | present |
| | peel strength to human (N/25 mm) | 1.5 | 1.7 | 4.1 | 4.7 | 5.3 | 0.2 | 0.1 | 3.4 |
| | peeled state to human — pain | 0 | 0 | 0 | 1 | 0 | 0 | 0 | 2 |
| | adhesive residue | none | none | none | small stickiness | none | none | none | present |
| rabbit skin primary irritation (P.I.I.) | | 0.0 | 0.0 | 0.0 | 0.5 | 0.5 | 0.0 | 0.0 | 1.7 |

* In Table, "delami" shows a state in which the adhesive layer is separated from the support on peeling, and transferred onto adherend (SUS, human skin).

From Table 3, Example 6 of the present invention, in which the content of non-volatile hydrocarbon oil was 113 parts by weight per 100 parts by weight of the thermoplastic elastomer, showed low adhesiveness but was free of adhesive residue and skin irritation. In the adhesive property, it was clarified that each adhesive sheet of Examples 1-5 of the present invention showed low peel strength to stainless steel as compared to the silicone-based adhesive sheet of Comparative Example 4, but showed appropriate adhesiveness of at least an equivalent level of peel strength to human. On the other hand, skin irritation was found to be low as compared to the silicone-based adhesive sheet of Comparative Example 4. In addition, high adhesiveness was found in the adhesive sheets for skin of Examples 1-5 using liquid paraffin having particularly high kinematic viscosity and a thermoplastic elastomer having a high diblock copolymer content.

[Examples 7-11] Preparation of Adhesive Sheet for Skin

According to the formulation shown in Table 4, each component constituting the adhesive layer was measured. The constituent components of the adhesive layer are as follows.

(1) thermoplastic elastomer (styrene-isoprene-styrene block copolymer (SIS)/styrene-isoprene block copolymer (SI) mixture): "JSR SIS5505" (in Table 1, abbreviated as "5505", manufactured by JSR Corporation, SIS/SI ratio (weight ratio)=50/50, solution viscosity of 25 wt % toluene solution at 25° C.=1.05 Pa·s)

(2) medium molecular weight polyisobutylene: "Oppanol B50SF" (in Table 1, abbreviated as "B50SF", manufactured by BASF, viscosity average molecular weight=400,000)

(3) non-volatile hydrocarbon oil (liquid paraffin): "Hydrobrite HV" (manufactured by Fujichem Sonneborn, kinematic viscosity at 40° C.=247 $mm^2/s$)

First, medium molecular weight polyisobutylene was dissolved in heptane or hexane in the amount described in Table 4 relative to 100 parts by weight of the total amount of a thermoplastic elastomer, polyisobutylene and non-volatile hydrocarbon oil. To the aforementioned solution was added propyl acetate or ethyl acetate in the amount described in Table 4, a styrene-isoprene-styrene block copolymer (SIS)/styrene-isoprene block copolymer (SI) mixture was further dissolved, liquid paraffin was added and the mixture was stirred to give a coating solution for forming an adhesive layer.

The above-mentioned coating solution was applied to a silicone-treated poly(ethylene terephthalate) (PET) film (release liner) such that the thickness of the adhesive layer after drying was about 400 μm. After drying under the condition described in Table 4, a PET film (support) was laminated on a Surface of the adhesive layer, which was cut in the size of 15 cm×30 cm to give the object adhesive sheet for skin.

TABLE 4

| component | | | | Ex. 7 | Ex. 8 | Ex. 9 | Ex. 10 | Ex. 11 |
|---|---|---|---|---|---|---|---|---|
| thermo-plastic elastomer | styrene-isoprene-styrene block copolymer (SIS)/styrene-isoprene block copolymer (SI) mixture | product name | SIS/SI ratio | | | | | |
| | | | solution viscosity (Pa · s) | | | | | |
| | | 5505 | 50/50  1.05 | 21 | 21 | 21 | 21 | 21 |
| polyiso-butylene | | product name | viscosity average molecular weight | | | | | |
| | medium molecular weight | B50SF | 400,000 | 16 | 16 | 16 | 16 | 16 |
| polyisobutylene content (parts by weight/thermoplastic elastomer 100 parts by weight) | | | | 76 | 76 | 76 | 76 | 76 |
| non-volatile hydro-carbon oil | liquid paraffin | product name | viscosity*2 (mm²/s) | | | | | |
| | | Hydro-brite HV | 247 | 63 | 63 | 63 | 63 | 63 |
| non-volatile hydrocarbon oil content (parts by weight/thermoplastic elastomer 100 parts by weight) | | | | 300 | 300 | 300 | 300 | 300 |
| solvent used for preparation of coating solution for forming adhesive layer | | | | heptane/propyl acetate = 80 parts by weight/20 parts by weight | heptane/propyl acetate = 70 parts by weight/30 parts by weight | heptane/propyl acetate = 60 parts by weight/40 parts by weight | hexane/ethyl acetate = 70 parts by weight/30 parts by weight | hexane/ethyl acetate = 50 parts by weight/50 parts by weight |
| drying condition | | | | 95° C. × 35 min | 95° C. × 35 min | 95° C. × 35 min | 70° C. × 10 min + 90° C. × 20 min | 70° C. × 10 min + 90° C. × 20 min |

*1; Unless particularly indicated, the values in Table show contents (wt %) in adhesive layer.
*2 measured at 40° C.

[Experimental Example 3] Evaluation of Adhesive Property, Skin Irritation and State of Adhesive Layer Similar to the above-mentioned Experimental Examples 1 and 2, adhesive property and skin primary irritation were evaluated and the results are shown in Table 5. In addition, the state of bubble generation and the dispersion state of polyisobutylene in the adhesive layer were also observed, and the observation results are also shown in Table 5.

The adhesive sheet for skin of Example 3 which was prepared using toluene as a solvent in the preparation of a coating solution for forming adhesive layer, and a commercially available patch preparation containing rivastigmine were also evaluated in the same manner.

TABLE 5

| | component | Ex. 3 | Ex. 7 | Ex. 8 | Ex. 9 | Ex. 10 | Ex. 11 | commercially available rivastigmine-containing patch preparation |
|---|---|---|---|---|---|---|---|---|
| | bubble generation state | fine small amount | 1 mm-large size, small amount | 1 mm-large size, small amount | 1 mm-large size, small amount | 1 mm-large size, many | 1 mm-large size, many | — |
| | polyisobutylene dispersion state | fine | crude | partially crude | fine | partially crude | fine | — |
| adhesive property | peel strength to SUS (N/25 mm) | 2.5 | 4.2 | 3.5 | 2.6 | 3.9 | 3.1 | 21.4 |
| | peeled state to SUS — adhesive residue | ultra-thin | present | partial | none | partial | none | present |
| | peel strength to human (N/25 mm) | 4.1 | 5.2 | 4.5 | 4.0 | 4.8 | 4.2 | 3.8 |
| | peeled state to human — pain | 0 | 1 | 1 | 0 | 1 | 0 | 2 |
| | adhesive residue | none | present | stickiness | small stickiness | stickiness | small stickiness | present |
| | rabbit skin primary irritation (P.I.I.) | 0.0 | — | — | — | — | — | 2.9 |

* In Table, "—" means that evaluation was not conducted.

As shown in Table 5, the generation state of bubbles in the adhesive layer varies according to the solvent used for the preparation of a coating solution for forming an adhesive layer, and particularly many bubbles were generated when a hexane/ethyl acetate mixed solvent was used. It was clarified that, when a heptane/propyl acetate mixed solvent or a hexane/ethyl acetate mixed solvent was used, the dispersion state of polyisobutylene in the adhesive layer varies depending on the mixing ratio of the solvents and, when the ratio of the hydrocarbon solvent and the acetate solvent was of the same level, polyisobutylene was finely dispersed similar to the use of toluene as the solvent, as a result of which adhesive residue was small in amount and good adhesiveness was afforded. When the mixing ratio of acetate exceeds 50 wt % of the total amount of solvent, polyisobutylene was precipitated, and a coating solution for forming an adhesive layer could not be obtained.

[Examples 12-16, Comparative Examples 5-7]
Preparation of Percutaneous Absorption Preparation Containing Rivastigmine According to the formulation shown in Table 6, each component constituting the adhesive layer was measured. The constituent components of the adhesive layer are as follows.
(1) thermoplastic elastomer: styrene-isoprene-styrene block copolymer (SIS)/styrene-isoprene block copolymer (SI) mixture
(a) KRAYTON D1111 (in Table 1, abbreviated as "D111"); manufactured by Kraton, SIS/SI ratio (weight ratio)=85/15, solution viscosity of 25 wt % toluene solution at 25° C.=1.2 Pa·s
(b) KRAYTON D1119 (in Table 1, abbreviated as "D119"); manufactured by Kraton, SIS/SI ratio (weight ratio)=34/66, solution viscosity of 25 wt % toluene solution at 25° C.=0.34 Pa·s
(c) JSR SIS5505 (in Table 1, abbreviated as "5505"); manufactured by JSR Corporation, SIS/SI ratio (weight ratio)=50/50, solution viscosity of 25 wt % toluene solution at 25° C.=1.05 Pa·s
(2) polyisobutylene
(a) low molecular weight polyisobutylene: Oppanol B10SFN (in Table 1, abbreviated as "B10SFN"); manufactured by BASF, viscosity average molecular weight=40,000
(b) medium molecular weight polyisobutylene: Oppanol B50SF (in Table 1, abbreviated as "B50SF"); manufactured by BASF, viscosity average molecular weight=400,000
(3) non-volatile hydrocarbon oil: liquid paraffin
(a) KAYDOL; manufactured by Fujichem Sonneborn, kinematic viscosity at 40° C.=67 $mm^2/s$
(b) Hydrobrite HV; manufactured by Fujichem Sonneborn, kinematic viscosity at 40° C.=247 $mm^2/s$ First, polyisobutylene was dissolved in 70 parts by weight of toluene relative to 100 parts by weight of the total amount of a thermoplastic elastomer, polyisobutylene, liquid paraffin and rivastigmine. In the aforementioned solution was further dissolved a styrene-isoprene-styrene block copolymer (SIS)/styrene-isoprene block copolymer (SI) mixture, liquid paraffin and rivastigmine were added and the mixture was stirred to give a coating solution for forming an adhesive layer.

The above-mentioned coating solution was applied onto a silicone-treated poly(ethylene terephthalate) (PET) film (release liner) such that the content of rivastiymine in the adhesive layer after drying was 1.8 $mg/cm^2$. After drying in an oven at 100° C. for 40 min, a PET film (support) was laminated on a surface of the adhesive layer, which was cut in the size of 15 cm×30 cm to give the object percutaneous absorption preparation.

TABLE 6

| component | | | | | Ex. 12 | Ex. 13 | Ex. 14 | Ex. 15 | Ex. 16 | Com. Ex. 5 | Com. Ex. 6 | Com. Ex. 7 |
|---|---|---|---|---|---|---|---|---|---|---|---|---|
| thermoplastic elastomer | styrene-isoprene-styrene block copolymer (SIS)/styrene-isoprene block copolymer (SI) mixture | product name | SIS/SI ratio | solution viscosity (Pa · s) | | | | | | | | |
| | | D1111 | 85/15 | 1.2 | | | | | | 38 | | |
| | | D1119 | 34/66 | 0.34 | | | | | | | 9.5 | 8.6 |
| | | 5505 | 50/50 | 1.05 | 24 | 21 | 20 | 20 | 19 | | | |
| polyisobutylene | | product name | viscosity average molecular weight | | | | | | | | | |
| | low molecular weight | B10SFN | 40,000 | | | | | | | | 57 | 9.5 |
| | medium molecular weight | B50SF | 400,000 | | 6 | 9 | 15 | 20 | 19 | | | |
| polyisobutylene content (parts by weight/thermoplastic elastomer 100 parts by weight) | | | | | 25 | 43 | 75 | 100 | 100 | 0 | 600 | 110 |
| non-volatile hydrocarbon oil | liquid paraffin | product name | viscosity*2 ($mm^2/s$) | | | | | | | | | |
| | | KAYDOL | 67 | | | | | | | 57 | 28.5 | 76.9 |
| | | Hydrobrite HV | 247 | | 65 | 65 | 60 | 55 | 57 | | | |
| non-volatile hydrocarbon oil content (parts by weight/thermoplastic elastomer 100 parts by weight) | | | | | 271 | 310 | 300 | 275 | 300 | 150 | 300 | 894 |
| rivastigmine | | | | | 5 | 5 | 5 | 5 | 5 | 5 | 5 | 5 |

*1; Unless particularly indicated, the values in Table show contents (wt %) in adhesive layer.
*2 measured at 40° C.

[Experimental Example 4] Evaluation of Adhesive Property and Skin Irritation

Similar to the above-mentioned Experimental Examples 1, 2, adhesive property and skin irritation were evaluated. In Comparative Examples 6 and 7, according to the formulation shown in Table 6, each component constituting the adhesive layer was measured, and a sheet was prepared by the above-mentioned method. However, the adhesive layer could not be stably maintained, and the evaluation could not be performed.

[Experimental Example 5] In Vitro Skin Permeability Test

According to the method described in WO 2006/093139, the skin extracted from the abdomen of a male Wister rat (5-week-old) was set on a vertical Franz diffusion cell. Respective percutaneous absorption preparations of Examples 12-16 and commercially available rivastigmine-containing percutaneous absorption preparation ("Exelon Patch", manufactured by Novartis Pharma K.K.) were each punched out in a circular shape with area 1.0 cm$^2$ to give samples, which were attached to the rat skin on the diffusion cell (n=3-6). Using 10% by volume ethanol saline as a receptor side solution, the content of rivastigmine in the receptor solution was measured over time by high performance liquid chromatography (HPLC) under the following conditions.
<HPLC Measurement Conditions>
HPLC system: high performance liquid chromatograph (LC2010C) manufactured by SHIMADZU CORPORATION
column: ODS, 4.6 mmφ×15 cm, 5 μm
column temperature: 25° C.
mobile phase: buffer/methanol=50/50 (volume ratio)
(buffer; 5.0 mM sodium 1-heptane sulfonate, 1% by volume phosphoric acid)
detection wavelength: 220 nm
flow: 0.8 mL/min From the above-mentioned quantitative results, the amount of rivastigmine that permeated the rat skin in for 24 hr after attachment of the sample was determined and the skin permeation amount of rivastigmine was compared between the percutaneous absorption preparations of Examples 12-16 and the commercially available percutaneous absorption preparation, and shown as a relative amount when the rivastigmine skin permeation amount in the commercially available percutaneous absorption preparation was 100.

The evaluation results of Experimental Examples 4, 5 are also shown in Table 7.

TABLE 7

|  |  | Ex. 12 | Ex. 13 | Ex. 14 | Ex. 15 | Ex. 16 | Com. Ex. 5 | commercially available rivastigmine-containing patch preparation |
|---|---|---|---|---|---|---|---|---|
| adhesive property | peel strength to SUS (N/25 mm) | 2.3 | 1.4 | 2.8 | 3.8 | 4.2 | 0.1 | 21.4 |
|  | peeled state to SUS adhesive residue | none | none | none | ultra-thin | ultra-thin | none | present |
|  | peel strength to human (N/25 mm) | 1.8 | 2.2 | 2.6 | 3.4 | 4.0 | 0.1 | 3.8 |
|  | peeled state to human pain | 0 | 0 | 0 | 0 | 1 | 0 | 2 |
|  | adhesive residue | none | sticky | none | small stickiness | small stickiness | none | present |
| rabbit skin primary irritation (P.I.I.) |  | — | — | 1.0 | — | — | — | 2.9 |
| skin permeation amount of drug after attachment of sample for 24 hr (relative amount when that of commercially available rivastigmine-containing patch preparation is 100) |  | 98 | 101 | 105 | 108 | 104 | — | 100 |

* In Table, "—" means that evaluation was not conducted.

From Table 7, it was found that the respective percutaneous absorption preparations of Examples 12-16 of the present invention showed at least an equivalent level of percutaneous absorbability as compared to the commercially available percutaneous absorption preparation and, in human, the preparations suppressed adhesive residue and pain on peeling and showed low skin irritation while exhibiting an equivalent level of adhesiveness.

[Examples 17-19] Preparation of Percutaneous Absorption Preparation Containing Rivastigmine According to the formulation shown in Table 8, each component constituting the adhesive layer was measured. The constituent components of the adhesive layer are as follows.
(1) thermoplastic elastomer (styrene-isoprene-styrene block copolymer (SIS)/styrene-isoprene block copolymer (SI) mixture): "JSR SIS5505" (in Table 1, abbreviated as "5505", manufactured by JSR Corporation, SIS/SI ratio (weight ratio)=50/50, solution viscosity of 25 wt % toluene solution at 25° C.=1.05 Pa·s)
(2) medium molecular weight polyisobutylene: "Oppanol B50SF" (in Table 1, abbreviated as "B50SF", manufactured by BASF, viscosity average molecular weight=400,000)
(3) non-volatile hydrocarbon oil (liquid paraffin): "Hydrobrite HV" (manufactured by Fujichem Sonneborn, kinematic viscosity at 40° C.=247 mm$^2$/s)

First, polyisobutylene was dissolved in the solvents described in Table 8 (heptane or hexane in Examples 18 and 19) relative to 100 parts by weight of the total amount of a thermoplastic elastomer, polyisobutylene, and non-volatile hydrocarbon oil. In the aforementioned solution was further dissolved a styrene-isoprene-styrene block copolymer (SIS)/styrene-isoprene block copolymer (SI) mixture (after addition of propyl acetate or ethyl acetate in Examples 18 and 19), liquid paraffin and rivastigmine were added and the mixture was stirred to give a coating solution for forming an adhesive layer.

The above-mentioned coating solution was applied onto a silicone-treated poly(ethylene terephthalate) (PET) film (release liner) such that the content of rivastigmine in the adhesive layer after drying was 1.8 mg/cm$^2$. After drying in an oven at 100° C. for 35 min, a PET film (support) was laminated on a surface of the adhesive layer, which was cut in the size of 15 cm×30 cm to give the object percutaneous absorption preparation.

Examples 17-19 and the commercially available percutaneous absorption preparation, and shown as a relative amount when the rivastigmine skin permeation amount in the commercially available percutaneous absorption preparation was 100.

The evaluation results of the above-mentioned Experimental Examples 6, 7 are also shown in Table 9.

TABLE 8

| component | | | | | Ex. 17 | Ex. 18 | Ex. 19 |
|---|---|---|---|---|---|---|---|
| thermoplastic elastomer | styrene-isoprene-styrene block copolymer (SIS)/styrene-isoprene block copolymer (SI) mixture | product name | SIS/SI ratio | solution viscosity (Pa · s) | | | |
| | | 5505 | 50/50 | 1.05 | 20 | 20 | 20 |
| polyisobutylene | | product name | viscosity average molecular weight | | 15 | 15 | 15 |
| | medium molecular weight | B50SF | 400,000 | | | | |
| | polyisobutylene content (parts by weight/thermoplastic elastomer 100 parts by weight) | | | | 75 | 75 | 75 |
| non-volatile hydrocarbon oil | liquid paraffin | product name | viscosity*$^2$ (mm$^2$/s) | | | | |
| | | Hydrobrite HV | 247 | | 60.5 | 60.5 | 60.5 |
| | non-volatile hydrocarbon oil content (parts by weight/thermoplastic elastomer 100 parts by weight) | | | | 303 | 303 | 303 |
| | rivastigmine | | | | 4.5 | 4.5 | 4.5 |
| | solvent used for producing preparation | | | | toluene = 70 parts by weight | heptane/propyl acetate = 52 parts by weight/35 parts by weight | hexane/ethyl acetate = 45 parts by weight/45 parts by weight |

*1; Unless particularly indicated, the values in Table show contents (wt %) in adhesive layer.
*$^2$measured at 40° C.

Experimental Example 6

Similar to the above-mentioned Experimental Example 1, adhesive property was evaluated. For comparison, a commercially available rivastigmine-containing percutaneous absorption preparation ("Exelon Patch", manufactured by Novartis Pharma K.K.) was also evaluated in the same manner.

[Experimental Example 7] In Vitro Skin Permeability Test (Use of Skin Resected from Human)

According to the method described in WO2006/093139, a skin sample resected from human was set on a vertical Franz diffusion cell. Respective percutaneous absorption preparations of Examples 17-19 and commercially available rivastigmine-containing percutaneous absorption preparation ("Exelon Patch", manufactured by Novartis Pharma K.K.) were each punched out in a circular shape with area 1.0 cm$^2$ to give samples, which were attached to the human skin on the diffusion cell (each n=6). Using 10% by volume ethanol saline as a receptor side solution, the content of rivastiymine in the receptor solution was measured over time in the same manner as in Experimental Example 5 by HPLC.

From the above-mentioned quantitative results, the amount of rivastigmine that permeated the human skin in for 24 hr after attachment of the sample was determined and the skin permeation amount of rivastigmine was compared between the percutaneous absorption preparations of

TABLE 9

| | | Ex. 17 | Ex. 18 | Ex. 19 | commercially available rivastigmine-containing patch preparation |
|---|---|---|---|---|---|
| adhesive property | peel strength to SUS (N/25 mm) | 2.4 | 2.6 | 3.2 | 21.4 |
| | peeled state to SUS | adhesive residue none | none | none | adhesive residue present |
| | peel strength to human (N/25 mm) | 3.0 | 3.0 | 2.9 | 3.8 |
| | peeled state to human | pain 0 adhesive residue none | 0 none | 0 none | pain 2 adhesive residue present |
| human skin permeation amount of drug after attachment of sample for 24 hr (relative amount when that of commercially available rivastigmine-containing patch preparation is 100) | | 101 | 110 | — | 100 |

* In Table, "—" means that evaluation was not conducted.

As shown in Table 9, the respective percutaneous absorption preparations of Example 17-19 of the present invention did not show adhesive residue or pain on peeling in human, while exhibiting the same level of adhesiveness as the commercially available rivastigmine-containing percutaneous absorption preparation. Also, in human skin permeability, at least an equivalent level of skin permeability as compared to a commercially available rivastigmine-containing percutaneous absorption preparation was observed.

Subsequently, Example of the second embodiment of the present invention is shown below.

[Examples 20-31, Comparative Examples 8-11]
Preparation of Adhesive Sheet for Skin According to the formulation shown in Table 10, each component constituting the adhesive layer was measured. The constituent components of the adhesive layer are as follows.
(1) thermoplastic elastomer: styrene-isoprene-styrene block copolymer (SIS)/styrene-isoprene block copolymer (SI) mixture
(a) KRAYTON D1111 (in Table 1, abbreviated as "Dill"); manufactured by Kraton Polymers, SIS/SI ratio (weight ratio)=85/15, solution viscosity of 25 wt % toluene solution at 25° C.=1.2 Pa·s
(b) KRAYTON D1119 (in Table 1, abbreviated as "D119"); manufactured by Kraton Polymers, SIS/SI ratio (weight ratio)=34/66, solution viscosity of 25 wt % toluene solution at 25° C.=0.34 Pa·s
(c) Quintac3520 (in Table 1, abbreviated as "QTC3520"); manufactured by Zeon Corporation, SIS/SI ratio (weight ratio)=22/78, solution viscosity of 25 wt % toluene solution at 25° C.=1.1 Pa·s
(d) JSR SIS5505 (in Table 1, abbreviated as "5505"); manufactured by JSR Corporation, SIS/SI ratio (weight ratio)=50/50, solution viscosity of 25 wt % toluene solution at 25° C.=1.05 Pa·s
(e) JSR SIS5229 (in Table 1, abbreviated as "5229"); manufactured by JSR Corporation, SIS/SI ratio (weight ratio)=80/20, solution viscosity of 25 wt % toluene solution at 25° C.=1.5 Pa·s (2) polyisobutylene
(a) low molecular weight polyisobutylene: Oppanol B10SFN (in Table 1, abbreviated as "B10SFN"); manufactured by BASF, viscosity average molecular weight=40,000
(b) low molecular weight polyisobutylene: Oppanol B15SFN (in Table 1, abbreviated as "B15SFN"); manufactured by BASF, viscosity average molecular weight=85,000
(c) high molecular weight polyisobutylene: Oppanol B80 (in Table 1, abbreviated as "B80"); manufactured by BASF, viscosity average molecular weight=800,000
(d) high molecular weight polyisobutylene: Oppanol B100 (in Table 1, abbreviated as "B100"); manufactured by BASF, viscosity average molecular weight=1,110,000
(e) high molecular weight polyisobutylene: Oppanol B150 (in Table 1, abbreviated as "B150"); manufactured by BASF, viscosity average molecular weight=2,600,000
(3) non-volatile hydrocarbon oil: liquid paraffin
(a) KAYDOL; manufactured by Fujichem Sonneborn, kinematic viscosity at 40° C.=67 $mm^2/s$
(b) Hydrobrite HV; manufactured by Fujichem Sonneborn, kinematic viscosity at 40° C.=247 $mm^2/s$ First, polyisobutylene was dissolved in 70 parts by weight of toluene relative to 100 parts by weight of the total amount of polyisobutylene, a thermoplastic elastomer, and liquid paraffin. In the aforementioned solution was further dissolved the thermoplastic elastomer, liquid paraffin was added and the mixture was stirred to give a coating solution for forming an adhesive layer.

The above-mentioned coating solution was applied to a silicone-treated poly(ethylene terephthalate) (PET) film (release liner) such that the thickness of the adhesive layer after drying was about 400 μm. After drying in an oven at 100° C. for 40 min, a PET film (support) was laminated on a surface of the adhesive layer, which was cut in the size of 15 cm×30 cm to give the object adhesive sheet for skin.

TABLE 10

| component | | | | | Ex. 20 | Ex. 21 | Ex. 22 | Ex. 23 | Ex. 24 | Ex. 25 | Ex. 26 | Ex. 27 | Ex. 28 |
|---|---|---|---|---|---|---|---|---|---|---|---|---|---|
| thermo-plastic elastomer | styrene-isoprene-styrene block copolymer (SIS)/styrene-isoprene block copolymer (SI) mixture | product name | SIS/SI ratio | solution viscosity (Pa·s) | | | | | | | | | |
| | | D1111 | 85/15 | 1.2 | 24 | | | | | | | | |
| | | D1119 | 34/66 | 0.34 | | | | | | | | | |
| | | QTC3520 | 22/78 | 1.1 | | | | | | | | 21 | |
| | | 5505 | 50/50 | 1.05 | | 24 | 24 | | | 12 | 21 | | |
| | | 5229 | 80/20 | 1.5 | | | | 20 | 8 | | | 16 | 11 |
| polyiso-butylene | | product name | viscosity average molecular weight | | | | | | | | | | |
| | low molecular weight | B10SFN | 40,000 | | 6 | 6 | 6 | | | | | | |
| | | B15SFN | 85,000 | | | | | 20 | 20 | 14 | 14 | 21 | 22 |
| | high molecular weight | B80 | 800,000 | | | | | | | 7 | 7 | | |
| | | B100 | 1,110,000 | | 6 | 6 | 6 | 10 | 10 | | | 11 | 11 |
| | | B150 | 2,600,000 | | | | | | | | | | |
| | polyisobutylene content (parts by weight/thermoplastic elastomer 100 parts by weight) | | | | 50 | 50 | 50 | 150 | 150 | 100 | 100 | 200 | 300 |
| non-volatile hydrocarbon oil | liquid paraffin | product name | viscosity[*2] ($mm^2/s$) | | | | | | | | | | |
| | | KAYDOL | 67 | | 64 | 64 | | | | | | | |
| | | Hydrobrite HV | 247 | | | | 64 | 50 | 50 | 58 | 58 | 52 | 56 |
| | non-volatile hydrocarbon oil content (parts by weight/thermoplastic elastomer 100 parts by weight) | | | | 267 | 267 | 267 | 250 | 250 | 276 | 276 | 325 | 509 |

TABLE 10-continued

| component | | | | | Ex. 29 | Ex. 30 | Ex. 31 | Com. Ex. 8 | Com. Ex. 9 | Com. Ex. 10 | Com. Ex. 11 |
|---|---|---|---|---|---|---|---|---|---|---|---|
| thermo-plastic elastomer | styrene-isoprene-styrene block copolymer (SIS)/styrene-isoprene block copolymer (SI) mixture | product name | SIS/SI ratio | solution viscosity (Pa·s) | | | | | | | |
| | | D1111 | 85/15 | 1.2 | | | | 40 | 43 | | |
| | | D1119 | 34/66 | 0.34 | | | | | | 10 | 9 |
| | | QTC3520 | 22/78 | 1.1 | | | | | | | |
| | | 5505 | 50/50 | 1.05 | 21 | 10.4 | 10.4 | | | | |
| | | 5229 | 80/20 | 1.5 | | 7 | 7 | | | | |
| polyiso-butylene | | product name | viscosity average molecular weight | | | | | | | | |
| | low molecular weight | B10SFN | 40,000 | | | | | | 6 | 60 | 10 |
| | | B15SFN | 85,000 | | 16 | 17.4 | 17.4 | | | | |
| | high molecular weight | B80 | 800,000 | | | | | | | | |
| | | B100 | 1,110,000 | | 8 | 8.7 | | | 6 | | |
| | | B150 | 2,600,000 | | | | 8.7 | | | | |
| polyisobutylene content (parts by weight/thermoplastic elastomer 100 parts by weight) | | | | | 114 | 150 | 150 | 0 | 28 | 600 | 111 |
| non-volatile hydrocarbon oil | liquid paraffin | product name | viscosity*[2] (mm²/s) | | | | | | | | |
| | | KAYDOL | 67 | | | | | 60 | 45 | 30 | 81 |
| | | Hydrobrite HV | 247 | | 55 | 56.5 | 56.5 | | | | |
| non-volatile hydrocarbon oil content (parts by weight/thermoplastic elastomer 100 parts by weight) | | | | | 262 | 325 | 325 | 150 | 105 | 300 | 900 |

*1; Unless particularly indicated, the values in Table show contents (wt %) in adhesive layer.
*[2] measured at 40° C.

[Comparative Example 12] Preparation of Silicone-Based Adhesive Sheet for Skin

According to the method described in [Example] of WO 2007/064407, a coating solution was prepared such that the composition after drying was the following composition, applied to a Teflon-treated poly(ethylene terephthalate) (PET) film (release liner) such that the weight per unit area after drying was 90 g/m², and dried.

A PET film (support) was laminated on a surface of the adhesive layer, which was cut in the size of 15 cm×30 cm to give the object adhesive sheet for skin.

<Coating Solution Composition>

| | |
|---|---|
| silicone-based adhesive ("Bio-PSA Q7-4301", manufactured by Dow Corning Corporation) | 98.9 (wt %) |
| silicone oil | 1.0 |
| vitamin E | 0.1 |

[Experimental Example 8] Adhesive Property Test (1) Preparation of Sample

The adhesive sheets for skin of Examples 20-31 and Comparative Examples 8-12 were each cut in the size of 25 mm×100 mm and used as samples.

(2) Peel Strength to Stainless Steel (SUS)

According to JIS Z0237:2009, each sample was attached to a stainless steel (SUS304) plate, and the stress when peeled in the 180° direction at a rate of 300 mm/min was measured using motorized test stand MX2-500N and digital force gauge ZP-50N manufactured by IMADA.

(3) Peel Strength to Human

According to JIS Z0237:2009, each sample was attached to a normal volunteer on the inside of forearm, and the stress when peeled in the 90° direction at a rate of 300 ram/min was measured using motorized test stand MX2-500N and digital force gauge ZP-50N manufactured by IMADA.

In addition, the pain felt when the sample was peeled was evaluated according to the following criteria <Evaluation Criteria>

0: pain is scarcely felt
1: slight pain is felt
2: considerable pain is felt

[Experimental Example 9] Primary Skin Irritation Test

The adhesive sheets for skin of Examples 20-31 and Comparative Examples 8-12 were each cut in the size of 2.5 cm square and used as samples.

Three days before the start of attachment, dorsal hair of kbs: JW female domestic rabbit (17-week-old) was shaven with an electric clipper, and each sample was attached to the skin (each n=3). Oil paper was placed thereon to cover the attached site, an underlap tape (manufactured by Nichiban Co., Ltd.) was wound from the chest to the whole abdomen, and a jacket for domestic rabbit (BJ03, manufactured by Bioresearch Center Co., Ltd.) was set thereon. After fixing for 24 hr, the sample was removed, and the level of skin irritation response was evaluated based on the method described in J. Pharmacol. Exp. Ther. 82, 377-390 (1944) for 1 hr, for 24 hr, for 48 hr and for 72 hr after the removal.

That is, after removal of the sample and after elapse of each of the above-mentioned times, erythema and eschar formation and edema formation were evaluated according to the following evaluation criteria, and scored. An average of respective evaluation points was determined, the primary evaluation value was calculated, and an average of the average evaluation value after elapse of each of the above-mentioned times was determined for each domestic rabbit and taken as a primary irritation index (P.I.I.). The P.I.I. value was 0 at the lowest and 8 at the highest, and the values are divided into 4 categories of primary skin irritation response shown in the above-mentioned Table 2.
<Evaluation Criteria of Skin Irritation Response>
[Formation of Erythema and Eschar]
  no erythema; 0 point
  very slight (barely perceptible level of) erythema; 1 point
  well-defined erythema; 2 points
  moderate to severe erythema; 3 points
  severe erythema to eschar formation of level preventing erythema scoring; 4 points
[Formation of Edema]
  no edema; 0 point
  very slight (barely perceptible level of) edema; 1 point
  slight edema (edges of area well defined by definite rising); 2 points
  moderate edema (raised approximately 1 mm); 3 points
  severe edema (raised more than 1 mm and extending beyond exposure area); 4 points
The results of the above-mentioned test are collectively shown in Table 11.

The adhesive sheets for skin of Comparative Examples 10, 11 failed to stably maintain the adhesive layer, and the above-mentioned test could not be performed.

provide sufficient adhesiveness to human. In addition, the adhesive sheet of Comparative Example 10 containing more than 500 parts by weight of polyisobutylene per 100 parts by weight of the thermoplastic elastomer, and the adhesive sheet of Comparative Example 11 containing more than 800 parts by weight of non-volatile hydrocarbon oil had difficulty in maintaining an adhesive layer, as mentioned above.

[Examples 32-37, Comparative Examples 13-16]
Preparation of Percutaneous Absorption Preparation Containing Rivastigmine According to the formulation shown in Table 12, each component constituting the adhesive layer was measured. The constituent components of the adhesive layer are as follows.
(1) thermoplastic elastomer
  Styrene-isoprene-styrene block copolymer (SIS)/styrene-isoprene block copolymer (SI) mixtures of the above-mentioned (a)-(e) were used.
(2) polyisobutylene
  Low molecular weight polyisobutylene of the above-mentioned (a), (b), and high molecular weight polyisobutylene of (c), (d) were used.

TABLE 11

| | | Ex. 20 | Ex. 21 | Ex. 22 | Ex. 23 | Ex. 24 | Ex. 25 | Ex. 26 | Ex. 27 | Ex. 28 | Ex. 29 | Ex. 30 | Ex. 31 | Com. Ex. 8 | Com. Ex. 9 | Com. Ex. 12 silicone |
|---|---|---|---|---|---|---|---|---|---|---|---|---|---|---|---|---|
| adhesive property | peel strength to SUS (N/25 mm) | 0.5 | 1.0 | 1.5 | 3.7 | 7.7 | 3.8 | 7.2 | 7.8 | 13.3 | 13.4 | 6.6 | 3.7 | 0.1 | 0.9 | 16.8 |
| | peeled state to SUS adhesive residue | none | none | none | none | ultra-thin | ultra-thin | ultra-thin | present | present | none | none | none | none | none | present |
| | peel strength to human (N/25 mm) | 0.5 | 1.0 | 2.0 | 2.5 | 6.2 | 5.5 | 6.8 | 7.4 | 10.0 | 9.8 | 4.5 | 3.6 | 0.1 | 0.2 | 3.4 |
| | peeled pain | 0 | 0 | 0 | 0 | 0 | 1 | 0 | 1 | 2 | 2 | 0 | 0 | 0 | 0 | 2 |
| | state to human adhesive residue | none | none | none | none | small stickiness | small stickiness | none | none | present | none | none | none | none | none | present |
| rabbit skin primary irritation (P.I.I.) | | 0.0 | 0.0 | 0.0 | 0.0 | 0.5 | 0.5 | 0.5 | 0.5 | 0.5 | 0.5 | 0.5 | 0.0 | 0.0 | 0.0 | 1.7 |

From Table 11, in the adhesive property, it was clarified that each adhesive sheet of Examples 20-31 of the present invention showed low peel strength to stainless steel as compared to the silicone-based adhesive sheet of Comparative Example 12, but showed appropriate adhesiveness of almost the equivalent level or above in the peel strength to human. On the other hand, skin irritation was found to be low as compared to the silicone-based adhesive sheet of Comparative Example 12. In addition, adhesiveness tended to improve in the adhesive sheets for skin of Examples 22-31 using liquid paraffin having high kinematic viscosity and a thermoplastic elastomer having a high diblock copolymer content. However, when the polyisobutylene content relative to the thermoplastic elastomer and the non-volatile hydrocarbon oil content relative to the thermoplastic elastomer became high, adhesive residue tended to occur on detachment.

The adhesive sheet of Comparative Example 8 which is free of polyisobutylene, and the adhesive sheet of Comparative Example 9, in which the content of non-volatile hydrocarbon oil was not more than 120 parts by weight per 100 parts by weight of the thermoplastic elastomer, failed to (3) non-volatile hydrocarbon oil
  Liquid paraffin of the above-mentioned (a), (b) was used.

First, polyisobutylene was dissolved in 70 parts by weight of toluene relative to 100 parts by weight of the total amount of polyisobutylene, a thermoplastic elastomer, liquid paraffin and rivastigmine. In the aforementioned solution was further dissolved a styrene-isoprene-styrene block copolymer (SIS)/styrene-isoprene block copolymer (SI) mixture, liquid paraffin and rivastigmine were added and the mixture was stirred to give a coating solution for forming an adhesive layer.

Then, the above-mentioned coating solution was applied to a silicone-treated poly(ethylene terephthalate) (PET) film (release liner) such that the content of rivastiymine in the adhesive layer after drying was 1.8 mg/cm$^2$. After drying in an oven at 100° C. for 40 min, a PET film (support) was laminated on a surface of the adhesive layer, which was cut in the size of 15 cm×30 cm to give the object percutaneous absorption preparation.

TABLE 12

| component | | | | Ex. 32 | Ex. 33 | Ex. 34 | Ex. 35 | Ex. 36 | Ex. 37 | Com. Ex. 13 | Com. Ex. 14 | Com. Ex. 15 | Com. Ex. 16 |
|---|---|---|---|---|---|---|---|---|---|---|---|---|---|
| thermoplastic elastomer | styrene-isoprene-styrene block copolymer (SIS)/styrene-isoprene block copolymer (SI) mixture | product name | SIS/SI ratio | solution viscosity (Pa · s) | | | | | | | | | |
| | | D1111 | 85/15 | 1.2 | | | | | | | 38 | 45 | | |
| | | D1119 | 34/66 | 0.34 | | | | | | | | | 9.5 | 8.6 |
| | | QTC3520 | 22/78 | 1.1 | | | | | | 20 | | | | |
| | | 5505 | 50/50 | 1.05 | 18 | 22.5 | 10.4 | 11.5 | 20 | | | | | |
| | | 5229 | 80/20 | 1.5 | | | 7 | 7.7 | | | | | | |
| polyisobutylene | | product name | | viscosity average molecular weight | | | | | | | | | | |
| | low molecular weight | B10SFN | | 40,000 | | | | | | | | 6 | 57 | 9.5 |
| | | B15SFN | | 85,000 | 8.1 | 9.6 | 17.4 | 19.2 | 13 | 13 | | | | |
| | high molecular weight | B80 | | 800,000 | | | | | 7 | 7 | | | | |
| | | B100 | | 1,110,000 | 4.1 | 4.8 | 8.7 | 9.6 | | | | 6 | | |
| | polyisobutylene content (parts by weight/thermoplastic elastomer 100 parts by weight) | | | | 68 | 64 | 150 | 150 | 100 | 100 | 0 | 27 | 600 | 110 |
| non-volatile hydrocarbon oil | liquid paraffin | product name | | viscosity*[2] (mm$^2$/s) | | | | | | | | | | |
| | | KAYDOL | | 67 | | | | | | | 57 | 43 | 28.5 | 76.9 |
| | | Hydrobrite HV | | 247 | 64.8 | 63.1 | 52.5 | 48.1 | 55 | 55 | | | | |
| | non-volatile hydrocarbon oil content (parts by weight/thermoplastic elastomer 100 parts by weight) | | | | 360 | 280 | 302 | 251 | 275 | 275 | 150 | 96 | 300 | 894 |
| | rivastigmine | | | | 5 | 5 | 4 | 4 | 5 | 5 | 5 | 5 | 5 | 5 |

*[1]; Unless particularly indicated, the values in Table show contents (wt %) in adhesive layer.
*[2] measured at 40° C.

[Experimental Example 10] Evaluation of Adhesive Property and Skin Irritation

The adhesive property of the percutaneous absorption preparations of Examples 32-37 and Comparative Examples 13-16 was evaluated in the same manner as in the above-mentioned Experimental Example 8, and the skin irritation of the percutaneous absorption preparations of Examples 32-37 was evaluated in the same manner as in the above-mentioned so Experimental Example 9. Also, a commercially available rivastigmine-containing percutaneous absorption preparation ("Exelon Patch" manufactured by Novartis Pharma) was also evaluated for the adhesive property and skin irritation in the same manner.

In Comparative Examples 15 and 16, according to the formulation shown in Table 12, each component constituting the adhesive layer was measured, and a sheet was prepared by the above-mentioned method. However, the adhesive layer could not be stably maintained, and the above-mentioned evaluation could not be performed.

[Experimental Example 11] In Vitro Skin Permeability Test

According to the method described in WO 2006/093139, the skin extracted from the abdomen of a male Wister rat (5-week-old) was set on a vertical Franz diffusion cell. Respective percutaneous absorption preparations of Examples 32-37, and the above-mentioned commercially available rivastigmine-containing percutaneous absorption preparation were each punched out in a circular shape (area 1.0 cm$^2$) to give samples and they were adhered onto the rat skin on the diffusion cell (n=3-6). Using 10% by volume ethanol saline as a receptor side solution, the content of rivastigmine in the receptor solution was quantified over time by high performance liquid chromatography (HPLC) under the following conditions.

<HPLC Measurement Conditions>

HPLC system: high performance liquid chromatograph (LC2010C) manufactured by SHIMADZU CORPORATION column: ODS, 4.6 mφ×15 cm, 5 μm column temperature: 25° C.

mobile phase: buffer/methanol=50/50 (volume ratio)

(buffer; 5.0 mM sodium 1-heptane sulfonate, 1% by volume phosphoric acid)

detection wavelength: 220 nm flow: 0.8 mL/min

From the above-mentioned quantitative results, the amount of rivastigmine that permeated the rat skin in for 24 hr after attachment of the sample was determined and the skin permeation amount of rivastigmine was compared between the percutaneous absorption preparations of Examples 32-37 and the commercially available percutaneous absorption preparation, and shown as a relative amount when the rivastigmine skin permeation amount in the commercially available percutaneous absorption preparation was 100.

The results of Experimental Examples 10, 11 are also shown in Table 13.

TABLE 13

|  |  | Ex. 32 | Ex. 33 | Ex. 34 | Ex. 35 | Ex. 36 | Ex. 37 | Com. Ex. 13 | Com. Ex. 14 | commercially available rivastigmine-containing patch preparation |
|---|---|---|---|---|---|---|---|---|---|---|
| adhesive property | peel strength to SUS (N/25 mm) | 1.5 | 2.1 | 3.9 | 8.3 | 2.7 | 6.5 | 0.1 | 1.0 | 21.4 |
|  | peeled state to SUS / adhesive residue | none | none | thin | present | ultra-thin | thin | none | none | present |
|  | peel strength to human (N/25 mm) | 2.6 | 4.1 | 4.9 | 5.6 | 3.5 | 7.1 | 0.1 | 0.2 | 3.8 |
|  | peeled state to human / pain | 0 | 1 | 1 | 1 | 0 | 1 | 0 | 0 | 2 |
|  | adhesive residue | present | none | none | small | small stickiness | stickiness | none | none | present |
| rabbit skin primary irritation (P.I.I.) | | 1.1 | 0.1 | 1.8 | 1.6 | 1.0 | 1.0 | — | — | 2.9 |
| skin permeation amount of drug after attachment of sample for 24 hr (relative amount when that of commercially available rivastigmine-containing patch preparation is 100) | | 104 | 103 | 101 | 103 | 102 | 91 | — | — | 100 |

* In Table, "—" means that evaluation was not conducted.

From Table 13, it was found that the respective percutaneous absorption preparations of Examples 32-37 of the present invention showed at least an equivalent level of percutaneous absorbability as compared to the commercially available percutaneous absorption preparation and, in human, the preparations suppressed adhesive residue and pain on peeling and showed low skin irritation while exhibiting an equivalent level of adhesiveness.

INDUSTRIAL APPLICABILITY

As described in detail in the above, the adhesive sheet for skin of the present invention shows appropriate adhesiveness to skin and low irritation to skin. A percutaneous absorption preparation of the present invention utilizing same has the aforementioned property and is also superior in percutaneous absorbability, and can be utilized for improving the property of the existing percutaneous absorption preparations, as well as development of a new percutaneous absorption preparation.

The present invention is based on patent application No. 2014-261231 filed in Japan, the contents of which are encompassed in full herein.

The invention claimed is:

1. An adhesive sheet for skin comprising a support and an adhesive layer formed on the support, wherein
the adhesive layer comprises at least a thermoplastic elastomer, non-volatile hydrocarbon oil and polyisobutylene having a viscosity average molecular weight of more than 100,000 and not more than 500,000,
a content of the non-volatile hydrocarbon oil is more than 120 parts by weight and not more than 800 parts by weight, per 100 parts by weight of said elastomer, and a content of said polyisobutylene is more than 3 parts by weight and not more than 500 parts by weight, per 100 parts by weight of said elastomer, and
a tackifier is not contained in the adhesive layer.

2. The adhesive sheet for skin according to claim 1, wherein the content of the polyisobutylene is more than 10 parts by weight and not more than 300 parts by weight, per 100 parts by weight of the thermoplastic elastomer.

3. The adhesive sheet for skin according to claim 2, wherein the content of the polyisobutylene is more than 20 parts by weight and not more than 100 parts by weight, per 100 parts by weight of the thermoplastic elastomer.

4. The adhesive sheet for skin according to claim 1, wherein the thermoplastic elastomer is a mixture of a triblock copolymer and a diblock copolymer, and a content of the diblock copolymer in the mixture is not less than 20 wt %.

5. The adhesive sheet for skin according to claim 4, wherein the content of the diblock copolymer in the mixture is not less than 30 wt %.

6. The adhesive sheet for skin according to claim 1, wherein the thermoplastic elastomer is a styrene-based block copolymer.

7. The adhesive sheet for skin according to claim 6, wherein the styrene-based block copolymer is a mixture of a styrene-isoprene-styrene block copolymer and a styrene-isoprene block copolymer.

8. The adhesive sheet for skin according to claim 1, wherein a 25 wt % toluene solution of the thermoplastic elastomer has a solution viscosity at 25° C. of not less than 0.5 Pa·s.

9. The adhesive sheet for skin according to claim 8, wherein the 25 wt % toluene solution of the thermoplastic elastomer has a solution viscosity at 25° C. of not less than 0.7 Pa·s.

10. The adhesive sheet for skin according to claim 1, wherein the non-volatile hydrocarbon oil has a kinematic viscosity at 40° C. of not less than 80 mm²/s.

11. The adhesive sheet for skin according to claim 1, wherein the content of the non-volatile hydrocarbon oil in the adhesive layer is not less than 30 wt % and not more than 80 wt %.

12. A percutaneous absorption preparation comprising the adhesive sheet for skin according to claim 1, and a drug or a pharmaceutically acceptable salt thereof comprised in the adhesive layer of the adhesive sheet.

13. The percutaneous absorption preparation according to claim 12, wherein the drug is rivastigmine.

14. An adhesive sheet for skin comprising a support and an adhesive layer formed on the support, wherein
the adhesive layer comprises at least a thermoplastic elastomer, non-volatile hydrocarbon oil and polyisobutylene having a viscosity average molecular weight of more than 100,000 and not more than 500,000, and
a tackifier is not contained in the adhesive layer.

15. A percutaneous absorption preparation comprising the adhesive sheet for skin according to claim 14, and a drug or a pharmaceutically acceptable salt thereof comprised in the adhesive layer of the adhesive sheet.

16. The percutaneous absorption preparation according to claim 15, wherein the drug is rivastigmine.

* * * * *